US008282916B2

(12) United States Patent
Meruelo et al.

(10) Patent No.: US 8,282,916 B2
(45) Date of Patent: Oct. 9, 2012

(54) TUMOR THERAPY WITH REPLICATION COMPETENT SINDBIS VIRAL VECTORS

(75) Inventors: Daniel Meruelo, Scarborough, NY (US); Jen-Chieh Tseng, Flushing, NY (US)

(73) Assignee: New York University, New York, NY (US)

( * ) Notice: Subject to any disclaimer, the term of this patent is extended or adjusted under 35 U.S.C. 154(b) by 187 days.

(21) Appl. No.: 12/390,096

(22) Filed: Feb. 20, 2009

(65) Prior Publication Data
US 2009/0214425 A1 Aug. 27, 2009

Related U.S. Application Data

(60) Provisional application No. 61/030,367, filed on Feb. 21, 2008.

(51) Int. Cl.
*A01N 63/00* (2006.01)
*A61K 48/00* (2006.01)

(52) U.S. Cl. .................. 424/93.2; 424/93.1; 514/44

(58) Field of Classification Search .......... 514/44; 424/93.1, 93.2
See application file for complete search history.

(56) References Cited

U.S. PATENT DOCUMENTS

| 7,303,798 | B2 | 12/2007 | Bavaro et al. | |
|---|---|---|---|---|
| 7,306,712 | B2 | 12/2007 | Watanabe et al. | |
| 7,306,792 | B2 * | 12/2007 | Meruelo | 424/93.2 |
| 2004/0102410 | A1 | 5/2004 | Meruelo | |
| 2007/0020236 | A1 | 1/2007 | Hurtado et al. | |

OTHER PUBLICATIONS

Tseng et al (J Nucl Med, 47: 1136-1143, 2006).*
Waehler et al (Nature Genetics, 8: 573-587, 2007).*
Wang K S, Kuhn R J, Strauss E G, Ou S, Strauss J H. High-affinity laminin receptor is a receptor for Sindbis virus in mammalian cells. J Virol. 66:4992-5001, 1992.
Strauss J H, Wang K S, Schmaljohn A L, Kuhn R J, Strauss E G. Host-cell receptors for Sindbis virus. Arch Virol. Suppl. 9:473-484, 1994.
Paolo Viacava, Antonio G. Naccarato, Paola Collecchi, Sylvie Menard, Vincent Castronovo and Generoso Bevilacqua. The Spectrum of 67-Kd Laminin Receptor Expression. In Breast Carcinoma Progression Journal of Pathology 182: 36-44, 1997.
Menard S, Tagliabue E, Colnaghi M N The 67 kDa laminin receptor as a prognostic factor in human cancer. Breast Cancer Res. Treat 52:137-145, 1998.
Martignone S, Menard S, Bufalino R, Cascinelli N, Pellegrini R, Tagliabue E, Andreola S, Rilke F, Colnaghi Mi. Prognostic significance of the 67-kilodalton laminin receptor expression in human breast carcinomas. J Natl. Cancer Inst. 85:398-402, 1993.
Basolo F, Pollina L, Pacini F, Fontanini G, Menard S, Castronovo V, Bevilacqua G. Expression of the Mr 67,000 laminin receptor is an adverse prognostic indicator in human thyroid cancer: an immunohistochemical study. Clin. Cancer Res. 2:1777-1780, 1996.
Sanjuan X, Fernandez P L, Miquel R, Munoz J, Castronovo V, Menard S, Palacin A, Cardesa A, Campo E. Overexpression of the 67-kD laminin receptor correlates with tumor progression in human colorectal carcinoma J Pathol. 179:376-380, 1996.
de Manzoni G, Verlato G, Tomezzoli A, Guglielmi A, Pelosi G, Ricci F, Di Leo A, Cordiano C. Study on Ki-67 immunoreactivity as a prognostic indicator in patients with advanced gastric cancer. Jpn J Clin. Oncol. 28:534-537, 1998.
Pelosi G, Pasini F, Bresaola E, Bogina G, Pederzoli P, Biolo S, Menard S, Zamboni G. High-affinity monomeric 67-kD laminin receptors and prognosis in pancreatic endocrine tumors. J Pathol. 183:62-69, 1997.
van den Brule F A, Castronovo V, Menard S, Giavazzi R, Marzola M, Belotti D, Taraboletti G Expression of the 67 kD laminin receptor in human ovarian carcinomas as defined by a monoclonal antibody, MluC5. Eur J Cancer 32A:1598-1602, 1996.
Taraboletti G, Belotti D, Giavazzi R, Sobel M E, Castronovo V. Enhancement of metastatic potential of murine and human melanoma cells by laminin receptor peptide G: attachment of cancer cells to subendothelial matrix as a pathway for hematogenous metastasis. J Natl. Cancer Inst. 85:235-240, 1993.
Ozaki I, K Yamamoto, T Mizuta, S Kajihara, N Fukushima, Y Setoguchi, F Morito, T Sakai. Differential expression of laminin receptors in human hepatocellular carcinoma. Gut 43:837-842, 1998.
van den Brule F A, Buicu C, Berchuck A, Bast R C, Deprez M, Liu F T, Cooper D N, Pieters C, Sobel M E, Castronovo V Expression of the 67-kD laminin receptor, galectin-1, and galectin-3 in advanced human uterine adenocarcinoma. Hum Pathol 27:1185-1191, 1996.
Levine B, Huang Q, Issacs J T, Reed J C and Hardwick J M. Conversion of lytic to persistent alphavirus infection by the bcl-2 cellular oncogene. Nature 361; 739-742, 1993.
Jan J T and Griffin D E. Induction of apoptosis by Sindbis virus occurs at cell entry and does not require virus replication J Virol. 73; 10296-10302, 1999.
Jan J T, Chatterjee S and Griffin D E. Sindbis virus entry into cells triggers apoptosis by activating sphingomyelinase, leading to the release of ceramide. J Virol. 74: 6425-6432, 2000.
Sawai et al., "Reducing cytotoxicity induced by Sindbis viral vectors", Mol Genet Metab. 1999, 67:36-42.
Griffin et al., "Regulators of apoptosis on the road to persistent alphavirus infection.", Ann. Rev., 1997, Microbiol. 51:565-592.
Liotta, L.A. et al., "Tumor Invasion and Metasteses Role of the Extracellular Matrix: Rhoads Memorial Award Lecture.", Cancer Research, 1986, 46:1-7.
Aznavoorian et al., 1992, Molecular Aspects of Tumor Cell Invasion and Metastasis, pp. 1368-1383.
Liotta et al., "Monoclonal antibodies to the human laminin receptor recognize structurally distinct sites.", 1985, Exp. Cell Res., 156:117-26.
Barsky et al., "Characterization of a Laminin Receptor From Human Breast Carcinoma Tissue", Breast Cancer Res. Treat., 1984, 4:181-188.
Terranova et al., "Laminin Receptor on Human Breast Carcinoma Cells,", Proc. Natl. Acad. Sci. USA, 1983, 80: 444-448.

(Continued)

*Primary Examiner* — Gerald Leffers, Jr.
*Assistant Examiner* — Magdalene Sgagias
(74) *Attorney, Agent, or Firm* — Fish & Richardson P.C.

(57) ABSTRACT

Disclosed herein are methods for treating a mammal harboring a solid tumor which expresses higher levels of High Affinity Laminin Receptors (LAMR) than normal cells of the same lineage comprising systematically administering to a mammal in need of such treatment a therapeutically effective amount of a Replication Competent (RC) Sindbis virus vector, wherein said vector encodes a suicide gene.

12 Claims, 4 Drawing Sheets

OTHER PUBLICATIONS

Horsburgh BC et al, Recurrent acyclovir-resistant herpes simplex in an immunocompromised patient; can strain differences compensate for loss of thymidine kinase in pathogenesis? J. Infect. Dis., 178 (3), 618-625, 1998.

Lacey SF et al, Analysis of mutations in the thymidine kinase genes of drug-resistant varicella-zoster virus populations using the polymerase chain reaction, J. Gen. Virol. 72 (PT 3), 623-630, 1991.

Perna NT et al, Genome sequence of enterohaemorrhagic *Escherichia coli* O157:H7, Nature 409 (6819), 529-533, 2001.

Chen et al., "Combination Suicide and Cytokine Gene Therapy for Hepatic Metastases of Colon Carcinoma: Sustained Antitumor Immunity Prolongs Animal Survival", Cancer Res. 1996, 56: 3758-3762.

Cormack, B. P. et al. (1966) FACS-optimized mutants of the green fluorescent protein (GFP). Gene 173:33-38.

de Wet, J.R., et al. (1987) Firefly luciferase gene: structure and expression in mammalian cells Mol. Cell Biol. 7 (2), 725-737.

Lorenz, W.W. et al. (1991) Isolation and expression of a cDNA encoding Renilla reinformis luciferase, Proc. Natl. Acad. Sci. U.S.A. 88 (10), 4438-4442.

MacLaren et al. "Repetitive, non-invasive imaging of the dopamine D2 receptor as a reporter gene in living animals.", Gene Therapy 6:785-791 (1999).

Yaghoubi et al. "Direct correlation between positron emission tomographic images of two reporter genes delivered by two distinct adenoviral vectors", Gene Therapy 8:1072-1080 ,2001.

Bredenbeek P.J. et al. (1993) Sindbis virus expression vectors: packaging of RNA replicons by using defective helper RNAs, J. Virol.; 67(11):6439-46.

Danks MK, Morton CL, Krull EJ, et al., Comparison of activation of CPT-11 by rabbit and human carboxylesterases for use in enzyme/prodrug therapy. Clin Cancer Res. 1999;5:917-924.

Austin EA, Huber BE. A first step in the development of gene therapy for colorectal carcinoma: cloning, sequencing, and expression of *Escherichia coli* cytosine deaminase. Mol Pharmacol. 1993:43:380-387.

Caruso M. Panis Y. Gagandeep S, Houssin D, Salzmann JL, Klatzmann D. Regression of established macroscopic liver metastases after in situ transduction of a suicide gene. Proc Natl Acad Sci U.S.A. 1993;90:7024-7028.

Sterman DH, Treat J, Litzky LA, et al. Adenovirus-mediated herpes simplex virus thymidine kinase/ganciclovir gene therapy in patients with localized malignancy: results of a phase I clinical trial in malignant mesothelioma. Hum Gene Ther. 1998;9:1083-1092.

Levis, R., Schlesinger, S. & Huang, H. V. Promoter for Sindbis virus RNA-dependent subgenomic RNA transcription. J Virol 64, 1726-33 (1990).

Raju, R. & Huang, H. V. Analysis of Sindbis virus promoter recognition in vivo, using novel vectors with two subgenomic mRNA promoters. J Virol 65,2501-10 (1991).

Hahn, C.S., Hahn, Y. S., Braciale, T. J. & Rice, C. M. Infectious Sindbis virus transient expression vectors for studying antigen processing and presentation. Proc Natl Acad Sci U.S.A. 89, 2679-83 (1992).

Pugachev, K. V., Mason, P. W., Shope, R. E. & Frey, T. K. Double-subgenomic Sindbis virus recombinants expressing immunogenic proteins of Japanese encephalitis virus induce significant protection in mice against lethal JEV infection. Virology 212, 587-94 (1995).

Tsuji, M. et al. Recombinant Sindbis viruses expressing a cytotoxic T-lymphocyte epitope of a malaria parasite or of influenza virus elicit protection against the corresponding pathogen in mice. J Virol 72, 6907-10 (1998.

Pierro, D. J., Myles, K. M., Foy, B. D., Beaty, B. J. & Olson, K. E. Development of an orally infections Sindbis virus transducing system that efficiently disseminates and expresses green fluorescent protein in *Aedes aegypti*. Insect Mol Biol 12, 107-16 (2003).

Unno, Y. et al. Oncolytic viral therapy for cervical and ovarian cancer cells by Sindbis virus AR339 strain. Clin Cancer Res 11, 4553-60 (2005).

Thomas, J. M., Klimstra, W. B., Ryman, K. D. & Heidner, H. W. Sindbis virus vectors designed to express a foreign protein as a cleavable component of the viral structural polyprotein. J Virol 77, 5598-606 (2003).

Frolova, E. et al. Formation of nsP3-specific protein complexes during Sindbis virus replication. J Virol 80, 4122-34 (2006).

Dilber MS, Abedi MR, Christensson B, et al. Gap junctions promote the bystander effect of herpes simplex virus thymidine kinase in vivo. Cancer Res. 1997;57:1523-1528.

Tseng JC, Levin B, Hirano T, Yee H, Pampeno C, Meruelo D. In vivo antitumor activity of sindbis viral vectors. J Natl Cancer Inst. 2002;94:1790-1802.

Tseng JC, Hurtado A, Yee H, et al. Using sindbis viral vectors for specific detection and suppression of advanced ovarian cancer in animal models. Cancer Res. 2004;64:6684-6692.

Serganova I, Doubrovin M, Vider J, et al. Molecular imaging of temporal dynamics and spatial heterogeneity of hypoxia-inducible factor-1 signal transduction activity in tumors n living mice. Cancer Res. 2004;64:6101-6108.

Blsasberg RG, Gelovani J. Molecular-genetic imaging: a nuclear medicine-based perspective. Mol Imaging. 2002;1:280-300.

Wen B, Burgman P, Zanzonico P, et al. A preclinical model for noninvasive imaging of hypoxia-induced gene expression: comparison with an exogenous marker of tumor hypoxia. Eur J Nucl Med Mol Imaging. 2004;31:1530-1538.

Agapov, et al, 1998. "Noncytopathic Sindvis virus RNA vectors for heterologous gene expression" Proc. Natl. Acad. Sci. USA 95(22): 12989-12994.

Frolov, et al,1996. "Alphavirus-based expression vectors: strategies and applications" Proc. Natl. Acad. Sci. USA 93 (21): 11371-11377.

Yazawa, et al, 2002. "Current progress in suicide gene therapy for cancer" World J. Surg. 26(7): 783-789.

* cited by examiner (A)
Wild-type Sindbis virus genomic RNA: single component

(B)
Replication-defective (RD) Sindbis viral vector system: dual components

(C)
Replication-capable (RC) Sindbis viral vector system: Single components

(D)
Replication-capable (RC) Sindbis viral vector system with safety feature: Single components

(A) RD-Sindbis/HSVtk

TUMOR THERAPY WITH REPLICATION COMPETENT SINDBIS VIRAL VECTORS

CROSS REFERENCE TO RELATED APPLICATIONS

The present application claims the benefit of U.S. Provisional Patent Application Ser. No. 61/030,367, filed Feb. 21, 2008, the contents of which are hereby incorporated by reference in their entirety.

The United States government has certain rights to this invention, by virtue of the funding received from grant CA1100687 from the National Institutes of Health.

FIELD OF THE INVENTION

The present invention is directed to methods to treat mammals suffering from tumors and to monitor anticancer therapy using Sindbis viral vectors and pharmaceutical formulations for use in the methods. In particular, the vectors are replication competent Sindbis Viral Vectors and the tumors are solid tumors expressing increased levels of High Affinity Laminin Receptors (LAMR) compared to normal cells of the same lineage.

BACKGROUND OF THE INVENTION

One type of gene therapy of tumors, gene-directed enzyme-prodrug therapy (GDEPT), holds considerable promise, although practical considerations limit its clinical applicability. These include the lack of acceptable noninvasive methods that are adaptable to humans for selective tumor targeting of the therapeutic genetic material. Sindbis virus is an oncolytic, alphavirus that selectively targets tumors through the 67-kDa laminin receptor (LAMR).

Gene therapy targets the genome of tumor cells as a basis for a highly selective and nontoxic anticancer therapy. To enhance selectively and specificity to the killing of cancer cells, several enzyme/prodrug systems—such as carboxylesterase/CPT-11 (1), cytosine deaminase/5-fluoro-cytosine (2), and herpes simplex virus thymidine kinase type 1 (HS-Vtk)/ganciclovir (GCV) (3,4)—have been developed for gene-directed enzyme-prodrug therapy (GDEPT). In this strategy, tumor cells are transduced with therapeutic genes that encode enzymes for specific conversion/activation of prodrugs, which are toxicologically inert at relatively high doses, into highly toxic metabolites for tumor killing.

In addition to a proper vector system, cancer GDEPT therapy would greatly benefit from a means to noninvasively monitor the GDEPT enzyme activity after vector treatments in vivo. Such capability could improve the Sindbis-based HSVtk/GCV GDEPT in clinical settings by providing important information to address 2 critical questions: (i) Do the vectors systemically target tumor cells and spare normal tissues? (i) Do the tumors have sufficient expression levels of the enzyme for tumor eradication by subsequent prodrug activation? In addition, monitoring during the therapy could facilitate optimizing the dose and dosing schedule of the prodrug to reduce unwanted side affects.

U.S. Pat. No. 7,306,712 discloses that vectors based on Sindbis virus, a blood-borne alphavirus transmitted through mosquito bites, infect tumor cells specifically and systemically throughout the body. The tumor specificity of Sindbis vectors may be mediated by the 67-kDa high-affinity laminin receptor (LAMR), which is over expressed in several types of human tumors. Another advantageous property of Sindbis vectors for cancer therapy is that, without carrying cytotoxic genes, they have been shown to induce apoptosis in mammalian cells. Furthermore, as Sindbis vectors are capable of expressing very high levels of their transduced suicide genes in infected tumor cells, the efficient production of the enzymes for sufficient prodrug conversion is ensured.

U.S. patent application Ser. No. 10/920,030 discloses methods and compositions for detecting cancer cells and monitoring cancer therapy using replication defective Sindbis virus vectors.

U.S. Pat. No. 7,303,798 discloses novel defective Sindbis virus vectors and their use in treating tumors in mammals.

SUMMARY OF THE INVENTION

The present inventors have unexpectedly discovered that replication competent (RC) Sindbis viral vectors have enhanced anti-tumor and cancer therapy monitoring activities when used with tumors which express higher levels of LAMR than normal cells of the same lineage. The RC Sindbis virus vectors are based on the mut-4 replication defective Sindbis virus vector disclosed in the '798 patent.

In one aspect, the present invention provides a method for treating a mammal harboring a solid tumor which expresses higher levels of High Affinity Laminin Receptors (LAMR) than normal cells of the same lineage comprising systematically administering to a mammal in need of such treatment a therapeutically effective amount of a Replication Competent (RC) Sindbis virus vector, wherein said vector encodes a suicide gene.

In another aspect, the present invention provides a method for monitoring anti-cancer therapy in a mammal harboring a solid tumor which expresses higher levels of LAMR than normal cells of the same lineage comprising administering to a mammal in need of such treatment a diagnostically effective amount of a Replication Competent (RC) Sindbis virus vector comprising a gene encoding a detectable label, and determining the amount of cancer cells in the body of said mammal, wherein the amount of cancer cells is proportional to the amount of label produced by said cancer cells and said vector encodes a suicide gene.

In a further aspect, the present invention provides a method for identifying cancer cells which expresses higher levels of LAMR than normal cells of the same lineage in the body of a mammal comprising administering to a mammal in need of such treatment a diagnostically effective amount of a mut-4 RC Sindbis virus vector comprising a gene encoding a detectable label, and assaying for said label, wherein said cell is a cancer cell if it expresses said label and said vector encodes a suicide gene.

In a still further aspect, the present invention provides a method for determining the amount of cancer cells which expresses higher levels of LAMR than normal cells of the same lineage in the body of a mammal comprising the steps of (a) administering to a mammal in need of such treatment a diagnostically effective amount of a mut-4 RC Sindbis virus vector comprising a gene encoding a detectable label, and (b) determining the amount of said detectable label, wherein the amount of cancer cells in the body of said mammal is proportional to the amount of said label and said vector encodes a suicide gene.

In yet another aspect, the present invention provides a Replication Competent mut-4 Sindbis virus vector, wherein said vector encodes a suicide gene.

In a still further aspect, the present invention provides a pharmaceutical formulation or dosage form for administration to a mammal suffering from a solid tumor which expresses higher levels of LAMR than normal cells of the same lineage comprising a mut-4 RC Sindbis virus vector and a pharmaceutically acceptable carrier or diluent, wherein said vector further comprises a suicide gene.

These and other aspects of the present invention will be apparent to those of ordinary skill in the art in light of the present description and drawings.

DETAILED DESCRIPTION OF THE INVENTION

Figure 1:
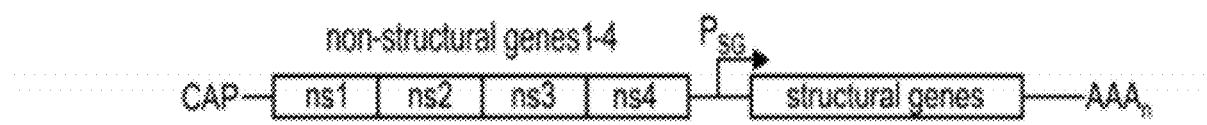
FIG. 1(A-D). Various Sindbis vector systems. (A) The wild-type Sindbis virus RNA genome has two major groups of genes: non-structural genes on the 5' side and structural genes on the 3' side. (B) The conventional two-component replication defective (RD) system contains a replicon RNA for therapeutic gene expression, and a helper RNA to provide structural genes for vector production. (C) A replication-capable (RC) vector system with integrated structural genes. (D) a RC vector system with a suicide gene fused in-frame with the ns3 gene to achieve "controlled" vector propagation and replication in tumor cells. The ns3 gene encodes a protein which is critical for viral replication and survival.
Figure 1:
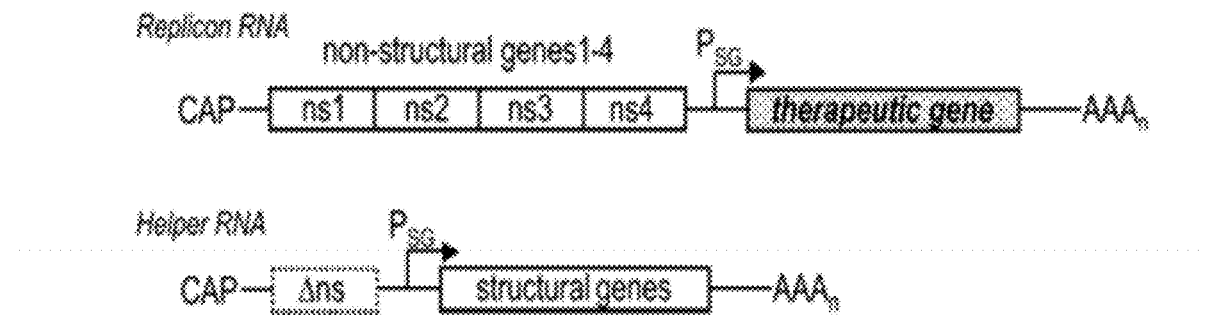
Figure 1:
Figure 1:
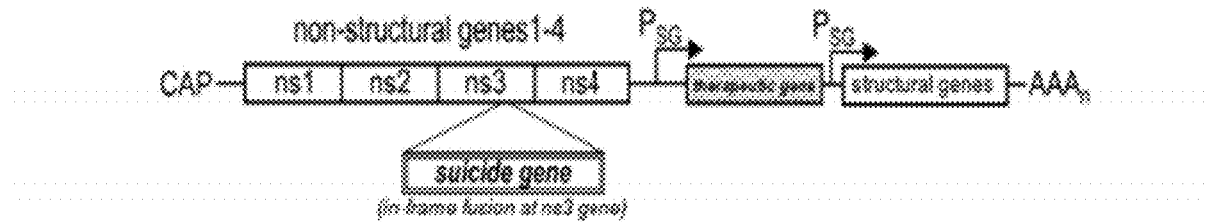

The instant invention takes advantage of the natural affinity of an alphavirus, particularly Sindbis virus, for tumor cells, in particular, for solid tumors that express higher levels of high affinity laminin receptors (alternatively referred to herein as LAMR or HALR), as compared to normal cells of the same lineage. The term "high affinity laminin receptor" or "LAMR" has its ordinary meaning in the art, i.e., the Mr 67,000 laminin receptor that can function as the receptor for Sindbis virus entry into cells (Wang et al., J. Virol. 1992, 66:4992-5001; Strauss et al., Arch. Virol. Suppl. 1994, 9:473-84).

Accordingly, the present invention provides a method for treating a mammal (e.g. human) suffering from a tumor that expresses greater levels of high affinity laminin receptor (LAMR) compared to normal cells of the same lineage. The method comprises administering to a mammal harboring such a tumor an amount of a vector effective to treat the tumor, wherein the vector has a preferential affinity for LAMR and the vector genome comprises a single component.

While not bound by any particular theory, three sets of observations may account for the remarkable anti-tumor efficiency of Sindbis vector-based therapy of the present invention. First, the LAMR can function as the receptor for Sindbis virus entry into cells of most species (Wang et al., J. Virol., 1992, 66:4992-5001; and Strauss et al., Arch. Virol. Suppl., 1994, 9:473-484). Second, it is widely recognized that expression of the LAMR is markedly elevated in many types of cancers (Menard et al., Breast Cancer Res. Treat, 1998, 52:137-145). In fact, a significant correlation has been established between the increased expression of Mr 67,000 LAMR and cancers of the breast (Menard et al., 1998, supra; Paolo Viacava et al., J. Pathol., 1997, 182:36-44; Martignone et al., J. Natl. Cancer Inst., 1993, 85:398-402), thyroid (Basolo et al., Clin. Cancer Res., 1996, 2:1777-1780), colon (San Juan et al., J Pathol., 1996, 179:376-380), prostate (Menard S et al., Breast Cancer Res. Treat, 1998, 52:137-145), stomach (de Manzoni et al., Jpn J Clin. Oncol., 1998, 28:534-537), pancreas (Pelosi et al., J Pathol., 1997, 183:62-69), ovary (Menard et al., Breast Cancer Res. Treat, 1998, 52:137-145; and van den Brule et al., Eur J Cancer, 1996, 32A: 1598-1602.), melanocytes (Taraboletti et al., J Natl. Cancer Inst., 1993, 85:235-240), lung (Menard et al., Breast Cancer Res. Treat, 1998, 52:137-145), liver (Ozaki et al., Gut, 1998, 43:837-842), endometrium, and uterus (van den Brule et al., Hum Pathol, 1996, 27:1185-1191). Indeed, data on more than 4000 cases of different tumors from diverse organs studied by immunohistochemistry are all concordant with a role for HALR in invasiveness, metastasis, and tumor growth (Menard et al., Breast Cancer Res. Treat., 1998, 52:137-145). Sindbis vectors, which are naturally blood-borne, can easily travel through the circulation and specifically home to and target growing and metastatic tumors expressing increased levels of LAMR. Finally, Sindbis virus is well known to be highly apoptotic for mammalian cells (Levine et al., Nature 1993, 739-742; Jan et al. J Virol., 1999: 10296-10302; Jan et al. J Virol 2000 6425-6432). Cell death begins within a few hours of infection and by 48-96 hours virtually all infected cells are dead (Sawai et al., Mol Genet Metab. 1999, 67:36-42; Griffin et al., Ann. Rev., 1997, Microbiol. 51:565-592).

The Sindbis vectors of the present invention, do not infect normal cells to the same extent in vivo compared to tumor cells. This allows for a differential effect in vector therapy, e.g., infection by Sindbis vectors results in the death of tumor cells leading to tumor elimination without apparent deleterious effects to other tissues and organs of the treated subjects. This phenomenon may be explained by the observation that an increased number of LAMR in tumors versus normal cells leads to a high number of exposed or unoccupied receptors on tumor cells (Liotta, L. A. Cancer Research, 1986, 46:1-7; Aznavoorian et al., 1992, Molecular Aspects of Tumor Cell Invasion and Metastasis, pp. 1368-1383). For example, it has been demonstrated that breast carcinoma and colon carcinoma tissues contain a higher number of exposed (unoccupied) LAMR compared to benign lesions (Liotta et al., 1985, Exp. Cell Res., 156:117-26; Barsky et al., Breast Cancer Res. Treat., 1984, 4:181-188; Terranova et al., Proc. Natl. Acad. Sci. USA, 1983, 80: 444-448). These excess unoccupied LAMR receptors on tumor cells, which are not found in normal cells, may be available for Sindbis virus binding, infection, and induction of cell death.

The invention advantageously provides a method for treating a mammal suffering from a tumor, in which the cells of the tumor express greater levels of LAMR compared to normal cells of the same lineage. The different levels of LAMRs result in target-mediated delivery, i.e., preferential binding of vectors of the invention to tumor cells. "Greater levels" of expression generally refer herein to levels that are expressed by tumor cells (as compared to non-tumor cells) and result in such preferential binding, e.g., at least a 3-fold greater binding, preferably at least a 30-fold greater binding and, most preferably at least a 300-fold greater binding. The increased level of expression in tumor cells can be evaluated on an absolute scale, i.e., relative to any other LAMR expressing non-tumor cells described, or on a relative scale, i.e., relative to the level expressed by untransformed cells in the same lineage as the transformed cancer cells (e.g., melanocytes in the case of melanoma; hepatocytes in the case of hepatic carcinoma; ovarian endothelial cells in the case of ovarian adenocarcinoma, renal endothelial or epithelial cells in the case of renal carcinoma).

As used herein, the term "infectious", "replication competent" or "replication capable", when used to describe a Sindbis virus vector RNA molecule, means an RNA molecule which is self-replicating and provides for transcription in a host cell. The term "replication", when used in conjunction with a Sindbis virus genomic RNA vector RNA molecule means production of full-length equivalents of (+)-strand RNA using (−)-strand RNA as a template.

As used herein, the term "tumor" refers to a malignant tissue comprising transformed cells that grow uncontrollably. Tumors include leukemias, lymphomas, myelomas, plasmacytomas, and the like; and solid tumors. Examples of solid tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, epidermoid carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, neuroglioma, and retinoblastoma. As noted above, the method of the invention depends on expression of LAMRs by cells of the tumor targeted for treatment.

The term "about" or "approximately" usually means within an acceptable error range for the type of value and method of measurement. For example, it can mean within 20%, more preferably within 10%, and most preferably still within 5% of a given value or range. Alternatively, especially in biological systems, the term "about" means within about a log (i.e., an order of magnitude) preferably within a factor of two of a given value.

The phrase "pharmaceutically acceptable", as used in connection with compositions of the invention, refers to molecular entities and other ingredients of such compositions that are physiologically tolerable and do not typically produce untoward reactions when administered to a human. Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "therapeutically effective" when applied to a dose or an amount refers to that quantity of a compound or pharmaceutical composition that is sufficient to result in a desired activity upon administration to a mammal in need thereof As used herein with respect to viral vectors of the invention, the term "therapeutically effective amount/dose" refers to the amount/dose of a vector or pharmaceutical composition containing the vector that is sufficient to produce an effective anti-tumor response upon administration to a mammal.

As disclosed in Ser. No. 10/920,030 the present inventors previously discovered and devised methods for detecting tumor cells and monitoring cancer therapy. The methods are based on the natural preference of Sindbis virus to infect human cancer cells that express higher level of 37/67-KDa laminin receptor (LAMR) than normal, non-cancerous cells.

Various Sindbis viral vectors for cancer gene therapy have been designed based on the RNA genome of wild-type virus (FIG. 1A). The wild-type genome contains two major parts. The first part, located on the 5' side of the genome, carries all of the non-structural genes (ns1, ns2, ns3, and ns4) and a packaging signal in the ns1 region. The expression of the ns1-4 genes leads to synthesis of the non-structural proteins nsp 1-4 that form the viral replicase. The replicase is necessary for expression of the structural genes in the second part of the genome at 3' side for virus formation. In order to do so, the replicase specifically recognizes a short stretch of sequences between the non-structural and structural genes, called the sub-genomic promoter ($P_{SG}$). One structural protein, the capsid protein, specifically recognizes the packaging signal at the ns1 region and picks it up to form viral particles with the rest of the structural proteins.

FIG. 1B depicts the conventional design of a replication defective Sindbis viral vector that is capable of efficient delivery of therapeutic genes while being unable to propagate and generate more vector particles. This particular system has two components. Replicon RNA contains all of the non-structural genes, while the structural genes are replaced with the therapeutic gene to be delivered. In order to generate vector particles, the structural genes are provided in trans using a helper RNA, the second component of this system. Unlike replicon RNA, the helper RNA contains the non-structural genes and lacks the packaging signal. Therefore, the produced vector particles only carry replicon RNA with the gene of interest.

One major advantage of such conventional dual-component vector systems is that the produced vector particle is replication-defective (RD) and is safer for clinical use. However, this advantage may become a significant drawback for cancer genes therapy. The goal of cancer gene therapy is to infect the majority of tumor cells and deliver the therapeutic genes for tumor detection or eradication. To achieve this goal using a replication-defective system may require a repetitive treatment regime and high doses of vectors. In some cases, such high doses may not be easily obtained using a replication defective system.

On the other hand, a Sindbis vector system that is capable of "controlled" replication and propagation is of great interest for cancer gene therapy. Such a replication-capable (RC) system should comprise a single-component to ensure efficient propagation of the vector in the tumor. That is, the system does not require a helper component for replication. One major benefit of such a system is that fewer treatments would be required and a lower dose should be sufficient to achieve successful therapeutic outcomes while retaining the same tumor targeting capability as RD vectors. Preferably, a safety mechanism is incorporated in the vector to ensure that the vector is eliminated in order to prevent unwanted toxicity, if any, associated with the propagation of the vector.

The present invention provides a replication-capable (RC) Sindbis viral vector (FIG. 1C) which was tested to see if a single-component system performed better than the conventional dual-component system. Instead of using a separate helper RNA vector to carry the structural genes, the structural genes are directly inserted into a conventional replicon vector, along with a dedicated sub-genomic promoter following the therapeutic gene. The dedicated second promoter guarantees that the efficient expression of the structural genes for high-level vector production occurs. A simple dual-promoter RC system was first developed in order to study the function of the sub-genomic promoter in mammalian cells (5,6). This type of RC system was later used to deliver antigen encoding genes for vaccination purposes (7-9). Since Sindbis virus infects mosquito cells, a simple RC system was also used to study Sindbis virus spreading in mosquitoes (10). In light of the present inventors' discovery that RD Sindbis vectors can target tumors in living animals, a single-component RC Sindbis vector has been used to detect/treat tumors in mouse tumor models (11). However, instead of using a dedicated sub-genomic promoter, the prior art RC system used a cleavable component to release the reporter protein from the structural proteins and, therefore, significantly reduced the titer of vector production (12).

Figure 2:
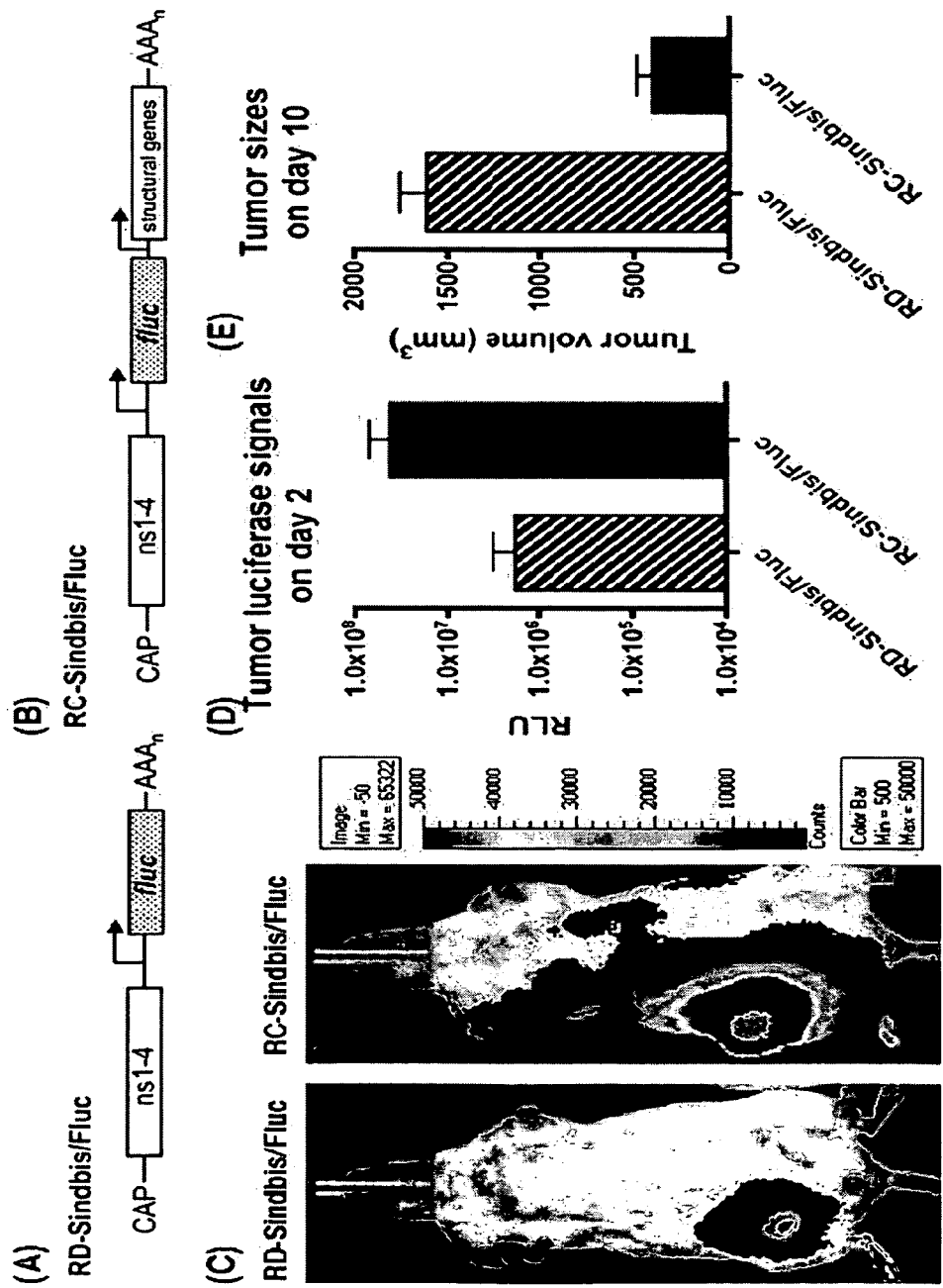
FIG. 2 (A-E). Replication-capable (RC) Sindbis virus vectors show superior tumor targeting and killing over conventional replication-defective (RD) systems. (A and B) Design of conventional RD-Sindbis/Fluc and a prototype RC-Sindbis/Fluc both carrying the firefly luciferase gene as reporter. (C) Bioluminescent imaging of tumor-bearing mice that received two consecutive daily treatments of RD- or RC-Sindbis/Fluc. The first dose was on day 0 and the last dose was on day 1. Subcutaneous BHK tumors were implanted on the right hind limb. (D) Quantitative representation of tumor signals after two consecutive treatments on day 2. (E) Tumor volume measured on day 10.

FIG. 2 shows the results of an experiment comparing the anti-tumor activity of replication defective (RD, FIG. 2A) and replication competent (RC, FIG. 2B) Sindbis virus vectors. In this set of experiments, a subcutaneously induced BHK tumor model (on the right hind limb of SCID mice) was used to test and compare these two vector systems. In order to evaluate specific tumor targeting and elimination in this model, both vector systems carry a firefly luciferase gene as a reporter. The bioluminescent signals generated in the tumors can be easily detected and analyzed using the IVIS™ imaging system. Mice received only two consecutive treatments of RD or RC vectors via systemic (intravenous) injections on a day 0 and day 1. No further treatment was administrated. FIG. 2C depicts the imaging result on day 2 and FIG. 2D quantitatively shows the level of bioluminescent signals in tumors that directly reflects vector infection level. The data indicate that the RC vector system has about a 30 fold increase in infectivity compared to the conventional RD vector system. Higher infectivity is also reflected in enhanced tumor killing as evidenced by tumor size reduction on day 10 (FIG. 2E).

These data provide proof-of-concept results in support of the use of a RC Sindbis vector system for cancer gene therapy. The capability of the RC vector to propagate and spread to the tumor dramatically enhances the ability of Sindbis vectors to target and kill cancer cells. The data also show that the same level of tumor detection can be achieved using a lower range of effective doses of the RC vector compared to conventional RD vectors. In the example depicted in FIG. 2, $10^6$ RD or RC vector particles were intravenously administered into mice. The signals from tumors treated with the RC vectors were about 30 fold higher than the RD signals. Therefore, the same imaging intensity in tumors was achieved using a lower dose ($10^4$ to $10^5$) of RC vectors. Interestingly, no toxicity was associated with this prototype RC vector administered at $10^6$ level and no bioluminescent signals, except in residual tumors, were observed in animals up to 20 days after vector injections, suggesting that using the same level of RC vector, as high as $10^6$ per dose, should not cause side effects. The higher dose is useful not only for detecting small lesions but also for better tumor killing and therapeutic effects. Since humans are about 1000 times the body weight of mice, the expected range of effective amounts for humans will range between about $10^7$ and about $10^{10}$ particles per dose. The lower range ($10^7$-$10^8$) is sufficient to detect tumor masses and higher range ($10^8$-$10^{10}$) are better for tumor eradication.

For use in the present invention, the RC Sindbis virus vectors can be produced as described in U.S. Pat. Nos. 7,306,712 and 7,303,798 and in the example below. This involves the described in vitro transcription/electroporation method.

However, as mentioned above, a safety mechanism significantly reduces the risk, if any, of toxicity by controlling the propagation of the RC vector system. In a preferred embodiment, a "suicide gene" is incorporated into one of the Sindbis virus non-structural genes that are essential for viral propagation and survival. FIG. 1C depicts the concept of such a design. A suicide gene, which encodes an enzyme capable of activating inert prodrugs into cytotoxic metabolites, is fused in frame with the ns3 gene to ensure co-expression with non-structural protein 3, an essential component of viral replicase. A particular region of the ns3 gene has been shown to be suitable for fusion without compromising the function of nsp3. Therefore, by such design the RC vector is genetically tagged with this safety mechanism which can shut-off vector propagation by killing the vector producing cell during or after the treatment regime.

In addition to serving as a safety feature, the fused suicide gene provides another advantage. The tumor cells that are selectively infected by the vector are more susceptible and sensitive to the prodrug treatment, since they would not only face the killing imposed by Sindbis infection, but also are exposed to toxic metabolites as a result of prodrug activation. In this regard, it has been discovered that activated toxic metabolites can passively diffuse to neighboring uninfected tumor cells to further enhance tumor killing. This is called a "bystander effect". The bystander effect plays an important role in the eradication of surrounding untransduced (uninfected) tumor cells. This is caused by transmission of the activated prodrug from the transduced tumor cells (which may be only a small fraction of total tumor mass) to uninfected tumor cells. In the HSVtk/GCV system, the activated GCV is not membrane permeable because of its highly charged phosphate groups. However, it can be transferred to uninfected cells via the gap junctions or through the exchange of apoptotic vesicles that kill the surrounding untransduced tumor cells (14).

Several suicide genes and their appropriate prodrugs are available and suitable for use with the Sindbis virus vector in this embodiment. For example, as disclosed herein, a conventional Sindbis virus vector carrying a thymidine kinase gene isolated from herpes simplex virus (HSVtk) significantly enhanced tumor killing (FIG. 3A) (Horsburgh B C et al, Recurrent acyclovir-resistant herpes simplex in an immunocompromised patient; can strain differences compensate for loss of thymidine kinase in pathogenesis? J. Infect. Dis., 178 (3), 618-625, 1998). A specific prodrug, ganciclovir (GCV), has been developed to target HSVtk, and has been clinically approved for treatment of cytomegalovirus and herpes simplex virus infection in humans. (Ganciclovir, GCV, is marketed under the trade name CYTOVENE™ by Roche Laboratories Inc.)

Additional examples of suicide genes are thymidine kinase of Varicella Zoster virus (VZV-tk) (disclosed in Lacey S F et al, Analysis of mutations in the thymidine kinase genes of drug-resistant varicella-zoster virus populations using the polymerase chain reaction, J. Gen. Virol. 72 (PT 3), 623-630, 1991) and the bacterial gene cytosine deaminase (Perna N T et al, Genome sequence of enterohaemorrhagic *Escherichia coli* O157:H7, Nature 409 (6819), 529-533, 2001).

The prodrugs useful in the methods of the present invention are any that can be converted to a toxic product, i.e., toxic to tumor cells. A preferred prodrug is ganciclovir, which is converted in vivo to a toxic compound by HSV-tk (Chen et al., Cancer Res. 1996, 56: 3758-3762). Other representative examples of prodrugs include acyclovir, FIAU [1-(2-deoxy-2-fluoro-β-D-arabinofuranosyl)-5-iodouracil] (FIALURI-DINE™, Moravek Biochemicals and Radiochemicals), 6-methoxypurine arabinoside (converted by VZV-tk), and 5-fluorocytosine (converted by cytosine deaminise) (5-fluorocytosine, Roche).

Prodrugs, may be readily administered to patients by physicians having ordinary skill in the art. Using methods known in the field, such physicians would also be able to determine the most appropriate dose and route for the administration of the prodrug. For example, ganciclovir is preferably administered systemically (e.g. orally or parenterally) in a dose of about 1-20 mg/day/kg body weight; acyclovir is administered in a dose of about 1-100 mg/day/kg body weight, and FIAU is administered in a dose of about 1-50 mg/day/kg body weight.

Figure 3:
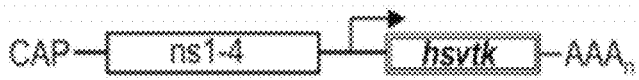
FIG. 3. (A-D). A suicide gene further enhances the therapeutic efficacy of Sindbis virus vectors. (A) Design of a conventional RD vector capable of expressing HSVtk for prodrug activation. (B) Bioluminescent imaging of ES2/Fluc ovarian cancer cells that express firefly luciferase for monitoring disease progression. SCID mice were inoculated with ES2/Fluc cells on day 0. Daily treatments with RD-Sindbis/HSVtk and GCV started on day 3. The combination of Sindbis virus vectors and the prodrug ganciclovir (GCV) significantly improved anti-tumor efficacy. (C and D) Quantitative representations of the imaging data.
Figure 3:
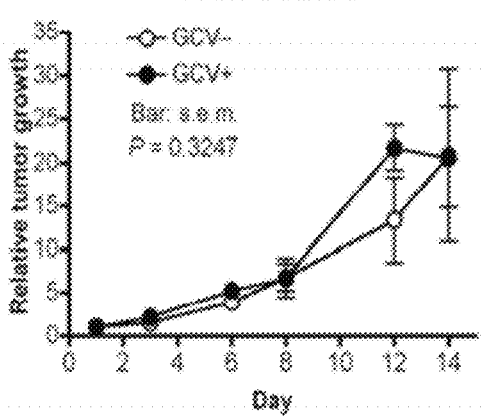
Figure 3:
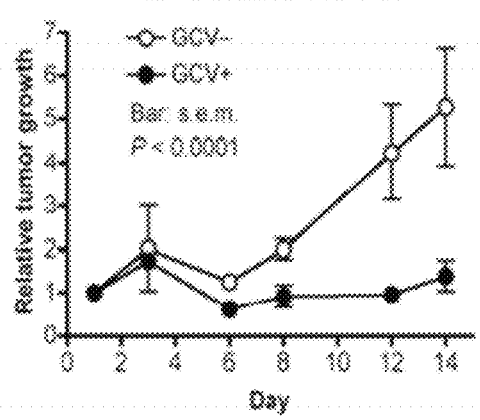

In the example below, SCID mice were intraperitoneally implanted with ES2 human ovarian cancer cells. In order to track and monitor disease progression, the ES2 cells were genetically engineered to express a firefly luciferase gene for bioluminescent imaging. Therefore, the bioluminescent signal intensity is proportional to the tumor load in these animals (FIG. 3B). Tumor-bearing mice were either mock treated or received daily treatments with a conventional RD-Sindbis/HSVtk vector. Some mice also received daily GCV treatments to determine if the prodrug enhanced tumor killing in conjunction with Sindbis vector treatment. Quantitative analysis indicated that, without HSVtk expression, unactivated GCV confers no therapeutic effect on tumor loading (FIG. 3C). On the contrary, GCV dramatically enhanced the Sindbis HSVtk vector treatments and suppressed tumor growth (FIG. 3D).

In an alternate embodiment, the vectors of the present invention can be used to detect cancer cells and monitor anti-cancer therapy. Previously, the present inventors used an optical bioluminescence imaging system and RD Sindbis virus vectors to detect tumor-specific targeting of Sindbis virus vectors in small animals (15, 16 and Ser. No. 10/920, 030). The advantages of bioluminescent imaging include short imaging time, low costs, and ease of use. However, optical imaging methods suffer from very substantial attenuation of the light signal and, thus, are not amenable to applications in large animals and in patients. Recent advances in optical and radionuclide imaging technology provide several methods for non-invasive monitoring of marker gene expression in living animals. On the other hand, radionuclide imaging methods such as g-camera, SPECT, and PET have excellent depth sensitivity and can detect accumulation of gene expression within the transfected tumors anywhere in the body and on the basis of gene expression imaging (17,18,19). A major advantage of PET is the ability to generate quantitative high spatial resolution, 3-dimensional images. When combined with other forms of tomographic imaging, such as CT or MRI, fusion images of functional and anatomic data provides more detailed in situ information of marker genes' expression and localization.

As disclosed in copending Ser. No. 10/920,030, the present inventors have discovered that imaging can be translated into photon counts produced by the detectable label delivered to cancer cells and that these are proportional to the amount of tumor cells that remain alive. Therefore, the present invention can be used to monitor anti-cancer therapy as follows. Patients can be administered a diagnostically-effective amount of the RC Sindbis vector of the present invention comprising a detectable label before the onset of treatment, and this value can be compared to one obtained upon administration of a diagnostically effective amount of a Sindbis virus comprising a detectable label after therapy has been completed. In this way, it is possible to determine the extent of tumor kill. Since only living tumor cells would contain the label, therapy would continue only until a minimal amount of label is detected.

Since Sindbis virus vectors are gene transfer vectors, the cancer cells are labeled using genetic markers incorporated into the RC Sindbis virus vectors. In this embodiment, the genes useful for live tumor monitoring or labeling include but are not limited to the Green Fluorescence Protein (GFP) gene, [Cormack, B. P. et al. (1966) FACS-optimized mutants of the green fluorescent protein (GFP). *Gene* 173:33-38] the Firefly luciferase (Fluc) gene, [de Wet, J. R., et al. (1987) Firefly luciferase gene: structure and expression in mammalian cells Mol. Cell Biol. 7 (2), 725-737], the Renilla luciferase (Rluc) gene [Lorenz, W. W. et al. (1991) Isolation and expression of a cDNA encoding Renilla reinformis luciferase, Proc. Natl. Acad. Sci. U.S.A. 88 (10), 4438-4442] and the dopamine-2 receptor ($D_2R$) gene. The use of the $D_2R$ gene as a reporter gene in living animals is disclosed in MacLaren et al. (Gene Therapy 6:785-791 (1999)) and Yaghoubi et al. (Gene Therapy 8:1072-1080 (2001)) These genes can be incorporated into the Sindbis virus vectors of the present invention using techniques well known to those of ordinary skill in the art, as described in Bredenbeek P. J. et al. (1993) (Sindbis virus expression vectors: packaging of RNA replicons by using defective helper RNAs, J. Virol.; 67(11):6439-46.)

Cells expressing the genetic markers of the present invention can be identified as follows: for the HSV-tk gene, the subject can be administered radiolabeled 9-[(4[$^{18}$F]fluro-3-hydroxymethylbutyl)guanine (FHBG), administered intravenously, about 6000 μCi/Kg body weight of the recipient, (commercially available from PET Imaging Science Center, U. of South California). Expression of HSV-tk activity in tumor cells results in the accumulation of radiolabeled FHBG and can be monitored by Positron Emission Tomography (PET). In vivo GFP expressing tumor cells can be monitored by fluoresence microscopic examination of tissue sections. Tissue sections of Fluc or Rluc expressing tumor cells can be monitored by Cooled Charge-Coupled Device (CCD) cameras in vivo (commercially available from Xenogen Corp., Alamenda, Calif.). $D_2R$ activity can be identified by administering 3-(2-[$^{18}$F]fluoroethyl)spiperone ([$^{18}$F]FESP) and monitored by PET.

A subject to whom the diagnostic compound of the present invention has been administered as an effective diagnostic monitor for a disease or disorder is preferably a human, but can be any animal, including a laboratory animal in the context of a clinical trial or screening or activity experiment. Thus, as can be readily appreciated by those of ordinary skill in the art, the methods and compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., ire., for veterinary medical use.

In summary, the single-component RC Sindbis vector system of the present invention dramatically enhances the tumor targeting, monitoring and killing capability of replication-capable Sindbis vectors, and incorporation of suicide genes provides an additional layer of protection to achieve "controlled" propagation in tumors and enhances tumor cell killing by RC Sindbis virus vectors.

In a preferred embodiment, the RC vectors are derived from the RD mut-4 vector disclosed in U.S. Pat. No. 7,303,798. The mut-4 vector is similar to the SinRep5 system (Invitrogen Corp.), except for changes in the amino acid sequences in the E2 protein. Since this protein is directly involved in vector binding and targeting to tumor cells, it is expected that RC vectors derived from the mut-4 vector will have the same improved binding capability as the RD vectors.

The construction of the RC mut-4 vector containing the HSV-tk gene is shown in Paper Example 1 below.

The present invention also provides pharmaceutical formulations or dosage forms for administration to mammals.

When formulated in a pharmaceutical composition, the vectors of the present invention can be admixed with a pharmaceutically acceptable carrier or excipient. The phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicles with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Alternatively, the carrier can be a solid dosage form carrier, including but not limited to one or more of a binder (for compressed pills), an encapsulating agent, a flavorant, and a colorant. Suitable pharmaceutical carriers are described in "Remington's Pharmaceutical Sciences" by E. W. Martin.

The preferred route of administration of the vectors of the present invention, for treatment and monitoring, is parenteral and most preferably systemic. This includes, but is not limited to intravenous, intraperitoneal, intra-arteriole, intramuscular, intradermal, subcutaneous, intranasal and oral. These routes of administration will permit homing of the vector to tumor cells wherein, only Sindbis virus is a blood-borne virus. Therefore, gene therapy vectors based on this virus have an advantage over other viral vectors that are not adapted to travel in the bloodstream. This property is largely responsible for the observation that systemic administration of Sindbis viral vectors by i.p. or i.v. injections, target and infect only tumors expressing greater amounts of LAMR than normal cells of the same lineage growing s.c., i.p., intrapancreatically, or in the lungs. Thus, the blood-borne nature of Sindbis viral vectors provides them with the capacity to treat malignancies and monitor cancer therapy.

The present invention is described below in examples which are intended to further describe the invention without limiting the scope therapy.

Materials and Methods
Vector Construction

The prototype RC-Sindbis/Fluc vector was constructed using the pSinRep5/Fluc plasmid as a backbone. In order to make the vector replication competent, a DNA segment containing a sub-genomic promoter and the Sindbis viral structural genes was excised from the ptRNA-DHBB plasmid (Invitrogen Corp., Carlsbad, Calif.) using NsiI and BamHI enzymes and then inserted into pSinRep5/Fluc at the StuI site. Therefore the constructed pSinRep5/Fluc-tBB plasmid has two independent sub-genomic promoters to drive expression of firefly luciferase and Sindbis viral structural proteins.

For construction of a RC vector with a suicide gene in the HSVtk gene was fused in-frame with the Ns3 gene at the SpeI site in pSinRep5/Fluc-tBB. The HSVtk gene (from the pORF-HSVtk plasmid, Invivogen, San Diego, Calif.) was inserted at this site to generate the pSinRep5-nsp3-HSVtk/Fluc-tBB plasmid.

Vector Preparation

The RC-Sindbis/Fluc vector was prepared using an in vitro transcription/electroporation method as described U.S. Pat. Nos. 7,306,712 and 7,303,798. The plasmid pSinRep5/Fluc-tBB was linearized using the NotI restriction enzyme. The linearized plasmid DNA was then used as template for in vitro transcription. The in vitro transcription was done in a total volume of 20 μL using a commercially available SP6 in vitro transcription kit (Ambion Inc., Austin, Tex.). Transcribed RNA (20 μL) was then electroporated into $6\times10^6$ BHK cells and cultured at 37° C. in a 10 cm dish containing 10 mL of αMEM (Invitrogen Corp.) with 10% FCS. The next day, the culture media was replaced with 9 mL of OptiMEM (Invitrogen). The OptiMEM was then harvested and stored at −80° C.

In Vivo Imaging

BHK tumors were induced in female SCID mice (Taconic, Germantown, N.Y.) by subcutaneous injection of 2 million BHK cells. Ten days later, on day 0, mice were split into two groups. One group of five mice received the first intravenous injection of $10^6$ particles of RD-Sindbis/Fluc, and the other group received the first i.v. injection of $10^6$ particles of RC-Sindbis/Fluc. The next day (day 1), both groups received a second dose ($10^6$) of i.v. treatments. Twenty-four hours later (day 2), tumor luminescence signals were measured using the IVIS® spectrum imaging system (Caliper LifeSciences, Hopkinton, Mass.) and tumor specific signals were analyzed using Living Image 3.0 software. Five minutes before imaging, 0.3 mL of 15 mg/mL D-luciferin (Promega, Madison, Wis.) was i.p. injected in order to generate bioluminescent signals. Tumor sizes were measured using calipers and volumes were calculated using the formula: $4\pi/3\times\text{length}\times\text{width}\times\text{height}$.

An ES-2/Fluc ovarian cancer model was used to test if the HSVtk suicide gene enhanced the therapeutic effects of Sindbis vectors. The prodrug GCV (CYTOVENE-IV®, The Roche Laboratories Inc.) enhanced the killing of Sindbis/tk-infected ES-2/Fluc cells in vivo, as determined by the IVIS® system, which is capable of non-invasive detection of bioluminescent signal generated by ES-2/Fluc tumors. SCID mice were inoculated with ES-2/Fluc on day 0. Daily GDEPT treatments involving i.p. injections of RD-Sindbis/tk and GCV (25 mg/Kg of body weight) were started on day 3. The Sindbis/tk −GCV group (n=5) received Sindbis/tk treatments but no GCV. The Sindbis/tk +GCV group (n=5) received both Sindbis/tk and GCV treatments. The Control group (n=5) was neither treated with Sindbis/tk nor GCV. The Control +GCV group (n=5) received no Sindbis/tk but was treated with GCV. Disease progression was monitored and the whole body photon counts were determined using the IVIS® system on days 1, 3, 6, 8, 12 and 14. Representative images of each treatment group are shown in FIG. 2.

In FIG. 2, tumor luciferase signals were higher and tumor volumes were lower using the RC vector compared to the RD vector. The average tumor luciferase signal in RC-treated mice was 43,970,000 photons, which was much higher than the average of 1,776,000 photons in RD-treated animals. The average tumor size of RC-treated tumors was 410 mm3 and for RD-treated tumor the average size was 1609 mm3.

PAPER EXAMPLE 1

Figure 4:
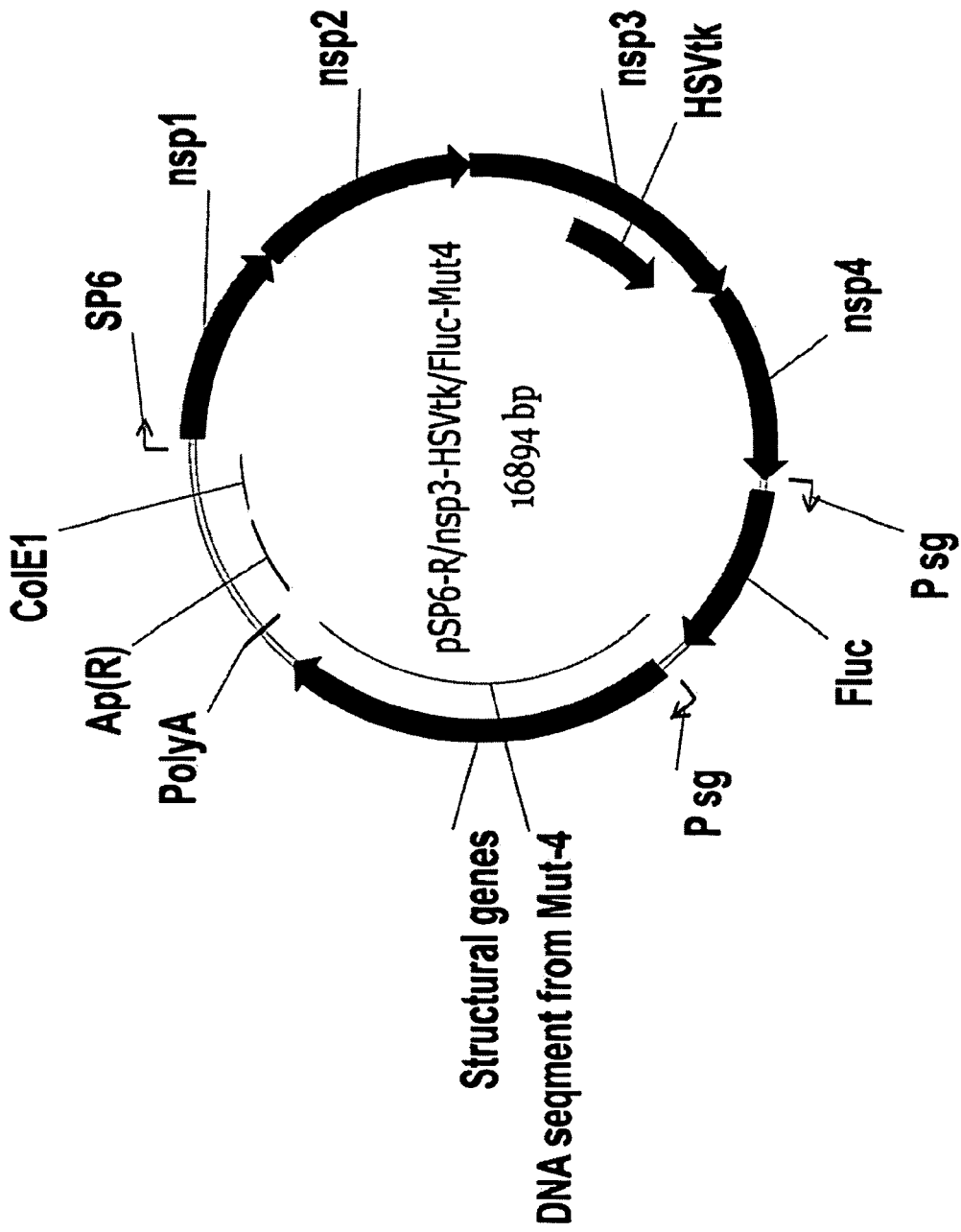
FIG. 4 is a map of the pSP6-R/NS3-HSVtk/Fluc-Mut4 plasmid. pSP6-R/NS3-HSVtk/Fluc-Mut4 is a Sindbis RC vector construction based on pSP6-R and Mut-4, which provides the replicase genes and structural genes respectively.

The plasmid pSP6-R/NS3-HSVtk/Fluc-Mut4 enclodes a Sindbis virus RC vector construction based on pSP6-R and Mut-4, which provide replicase genes and structural genes respectively. Its sequence is set forth in Appendix A and a map of the plasmid is shown in FIG. 4. In an alternate embodiment, the promoter is T7 (Ambun, Austin, Tex. ??) Its construction is described as follows.

A DNA segment containing a sub-genomic promoter and the Sindbis viral structural genes is excised from the pSP6-Mut4 plasmid (disclosed in U.S. Pat. No. 7,303,798) using NsiI and BamHI enzymes and then inserted into pSP6-R/Fluc at the PmlI site. In addition, the HSVtk gene fragment (from the pORF-HSVtk plasmid (Invivogen, San Diego, Calif.) is inserted at the SpeI site in the ns3 region on pSP6-R/Fluc-tBB to generate the pSP6-R/nsp3-HSVtk/Fluc-tBB plasmid. A map showing the pSP6-R/nsp3-HSVtk/Fluc-tBB plasmid is shown in FIG. 4 and its sequence is set forth in Appendix A below.

In FIG. 4, the location of the genes is set forth below:
Sindbis non-structural genes locations (bp):

| | |
|---|---|
| NS1 | 60-1979 (SEQ. ID NO.: 2) |
| NS2 | 1980-4100 (SEQ. ID NO.: 3) |
| NS3 | 4101-5261 and 6399-6878 (SEQ. ID NO.: 4) |
| NS4 | 6879-8729 (SEQ. ID NO.: 5) |
| First Psg | 8722-8734 (SEQ. ID NO.: 6) |
| Second Psg | 10766-10789 (SEQ. ID NO. 7) |
| Structural Genes: | 10833-14567 (SEQ. ID NO.: 8) |

In addition, the vector may also comprise a suicide gene, such as the thymidine kinase (TK) gene located within the NS3 gene (Nucleotide 5262-6398).

REFERENCES

1. Danks M K, Morton C L, Krull E J, et al., Comparison of activation of CPT-11 by rabbit and human carboxylesterases for use in enzyme/prodrug therapy. Clin Cancer Res. 1999; 5:917-924.
2. Austin E A, Huber B E. A first step in the development of gene therapy for colorectal carcinoma: cloning, sequencing, and expression of *Escherichia coli* cytosine deaminase. Mol Pharmacol. 1993:43:380-387.
3. Caruso M. Panis Y. Gagandeep S, Houssin D, Salzmann J L, Klatzmann D. Regression of established macroscopic liver metastases after in situ transduction of a suicide gene. Proc Natl Acad Sci U.S.A. 1993; 90:7024-7028.
4. Sterman D H, Treat J, Litzky L A, et al. Adenovirus-mediated herpes simplex virus thymidine kinase/ganciclovir gene therapy in patients with localized malignancy: results of a phase I clinical trial in malignant mesothelioma. Hum Gene Ther. 1998; 9:1083-1092.
5. Levis, R., Schlesinger, S. & Huang, H. V. Promoter for Sindbis virus RNA-dependent subgenomic RNA transcription. J Virol 64, 1726-33 (1990).
6. Raju, R. & Huang, H. V. Analysis of Sindbis virus promoter recognition in vivo, using novel vectors with two subgenomic mRNA promoters. J Virol 65, 2501-10 (1991).
7. Hahn, C. S., Hahn, Y. S., Braciale, T. J. & Rice, C. M. Infectious Sindbis virus transient expression vectors for studying antigen processing and presentation. Proc Natl Acad Sci U.S.A. 89, 2679-83 (1992).
8. Pugachev, K. V., Mason, P. W., Shope, R. E. & Frey, T. K. Double-subgenomic Sindbis virus recombinants expressing immunogenic proteins of Japanese encephalitis virus induce significant protection in mice against lethal JEV infection. Virology 212, 587-94 (1995).
9. Tsuji, M. et al. Recombinant Sindbis viruses expressing a cytotoxic T-lymphocyte epitope of a malaria parasite or of influenza virus elicit protection against the corresponding pathogen in mice. J Virol 72, 6907-10 (1998).
10. Pierro, D. J., Myles, K. M., Foy, B. D., Beaty, B. J. & Olson, K. E. Development of an orally infectious Sindbis virus transducing system that efficiently disseminates and expresses green fluorescent protein in *Aedes aegypti*. Insect Mol Biol 12, 107-16 (2003).
11. Unno, Y. et al. Oncolytic viral therapy for cervical and ovarian cancer cells by Sindbis virus AR339 strain. Clin Cancer Res 11, 4553-60 (2005).
12. Thomas, J. M., Klimstra, W. B., Ryman, K. D. & Heidner, H. W. Sindbis virus vectors designed to express a foreign protein as a cleavable component of the viral structural polyprotein. J Virol 77, 5598-606 (2003).
13. Frolova, E. et al. Formation of nsP3-specific protein complexes during Sindbis virus replication. J Virol 80, 4122-34 (2006).
14. Dilber M S, Abedi M R, Christensson B, et al. Gap junctions promote the bystander effect of herpes simplex virus thymidine kinase in vivo. Cancer Res. 1997; 57:1523-1528.
15. Tseng J C, Levin B, Hirano T, Yee H, Pampeno C, Meruelo D. In vivo antitumor activity of sindbis viral vectors. J Natl Cancer Inst. 2002; 94: 1790-1802.
16. Tseng J C, Hurtado A, Yee H, et al Using sindbis viral vectors for specific detection and suppression of advanced ovarian cancer in animal models. Cancer Res. 2004; 64:6684-6692.
17. Serganova I, Doubrovin M, Vider J, et al. Molecular imaging of temporal dynamics and spatial heterogeneity of hypoxia-inducible factor-1 signal transduction activity in tumors n living mice. Cancer Res. 2004; 64:6101-6108.
18. Blsasberg R G, Gelovani J. Molecular-genetic imaging: a nuclear medicine-based perspective. Mol Imaging. 2002; 1:280-300.
19. Wen B, Burgman P, Zanzonico P, et al. A preclinical model for noninvasive imaging of hypoxia-induced gene expression: comparison with an exogenous marker of tumor hypoxia. Eur J Nucl Med Mol Imaging. 2004; 31:1530-1538.

APPENDIX A pS6-R/nsp3-HSVtk/Fluc-Mut4 (SEQ ID NO. I

```
   1 ATTGACGGCG TAGTACACAC TATTGAATCA AACAGCCGAC CAATTGCACT
     TAACTGCCGC ATCATGTGTG ATAACTTAGT TTGTCGGCTG GTTAACGTGA

51 ACCATCACAA TGGAGAAGCC AGTAGTAAAC GTAGACGTAG ACCCCCAGAG
     TGGTAGTGTT ACCTCTTCGG TCATCATTTG CATCTGCATC TGGGGGTCTC

101 TCCGTTTGTC GTGCAACTGC AAAAAAGCTT CCCGCAATTT GAGGTAGTAG
     AGGCAAACAG CACGTTGACG TTTTTTCGAA GGGCGTTAAA CTCCATCATC

151 CACAGCAGGT CACTCCAAAT GACCATGCTA ATGCCAGAGC ATTTTCGCAT
     GTGTCGTCCA GTGAGGTTTA CTGGTACGAT TACGGTCTCG TAAAAGCGTA

201 CTGGCCAGTA AACTAATCGA GCTGGAGGTT CCTACCACAG CGACGATCTT
     GACCGGTCAT TTGATTAGCT CGACCTCCAA GGATGGTGTC GCTGCTAGAA

251 GGACATAGGC AGCGCACCGG CTCGTAGAAT GTTTTCCGAG CACCAGTATC
     CCTGTATCCG TCGCGTGGCC GAGCATCTTA CAAAAGGCTC GTGGTCATAG

301 ATTGTGTCTG CCCCATGCGT AGTCCAGAAG ACCCGGACCG CATGATGAAA
     TAACACAGAC GGGGTACGCA TCAGGTCTTC TGGGCCTGGC GTACTACTTT

351 TATGCCAGTA AACTGGCGGA AAAAGCGTGC AAGATTACAA ACAAGAACTT
     ATACGGTCAT TTGACCGCCT TTTTCGCACG TTCTAATGTT TGTTCTTGAA

401 GCATGAGAAG ATTAAGGATC TCCGGACCGT ACTTGATACG CCGGATGCTG
     CGTACTCTTC TAATTCCTAG AGGCCTGGCA TGAACTATGC GGCCTACGAC

451 AAACACCATC GCTCTGCTTT CACAACGATG TTACCTGCAA CATGCGTGCC
     TTTGTGGTAG CGAGACGAAA GTGTTGCTAC AATGGACGTT GTACGCACGG

501 GAATATTCCG TCATGCAGGA CGTGTATATC AACGCTCCCG GAACTATCTA
     CTTATAAGGC AGTACGTCCT GCACATATAG TTGCGAGGGC CTTGATAGAT

551 TCATCAGGCT ATGAAAGGCG TGCGGACCCT GTACTGGATT GGCTTCGACA
     AGTAGTCCGA TACTTTCCGC ACGCCTGGGA CATGACCTAA CCGAAGCTGT

601 CCACCCAGTT CATGTTCTCG GCTATGGCAG GTTCGTACCC TGCGTACAAC
     GGTGGGTCAA GTACAAGAGC CGATACCGTC CAAGCATGGG ACGCATGTTG

651 ACCAACTGGG CCGACGAGAA AGTCCTTGAA GCGCGTAACA TCGGACTTTG
     TGGTTGACCC GGCTGCTCTT TCAGGAACTT CGCGCATTGT AGCCTGAAAC

701 CAGCACAAAG CTGAGTGAAG GTAGGACAGG AAAATTGTCG ATAATGAGGA
     GTCGTGTTTC GACTCACTTC CATCCTGTCC TTTTAACAGC TATTACTCCT

751 AGAAGGAGTT GAAGCCCGGG TCGCGGGTTT ATTTCTCCGT AGGATCGACA
     TCTTCCTCAA CTTCGGGCCC AGCGCCCAAA TAAAGAGGCA TCCTAGCTGT

801 CTTTATCCAG AACACAGAGC CAGCTTGCAG AGCTGGCATC TTCCATCGGT
     GAAATAGGTC TTGTGTCTCG GTCGAACGTC TCGACCGTAG AAGGTAGCCA

851 CTTCCACTTG AATGGAAAGC AGTCGTACAC TTGCCGCTGT GATACAGTGG
     CAAGGTGAAC TTACCTTTCG TCAGCATGTG AACGGCGACA CTATGTCACC

901 TGAGTTGCGA AGGCTACGTA GTGAAGAAAA TCACCATCAG TCCCGGGATC
     ACTCAACGCT TCCGATGCAT CACTTCTTTT AGTGGTAGTC AGGGCCCTAG

951 ACGGGAGAAA CCGTGGGATA CGCGGTTACA CACAATAGCG AGGGCTTCTT
     TGCCCTCTTT GGCACCCTAT GCGCCAATGT GTGTTATCGC TCCCGAAGAA

1001 GCTATGCAAA GTTACTGACA CAGTAAAAGG AGAACGGGTA TCGTTCCCTG
     CGATACGTTT CAATGACTGT GTCATTTTCC TCTTGCCCAT AGCAAGGGAC

1051 TGTGCACGTA CATCCCGGCC ACCATATGCG ATCAGATGAC TGGTATAATG
     ACACGTGCAT GTAGGGCCGG TGGTATACGC TAGTCTACTG ACCATATTAC

1101 GCCACGGATA TATCACCTGA CGATGCACAA AAACTTCTGG TTGGGCTCAA
     CGGTGCCTAT ATAGTGGACT GCTACGTGTT TTTGAAGACC AACCCGAGTT

1151 CCAGCGAATT GTCATTAACG GTAGGACTAA CAGGAACACC AACACCATGC
     GGTCGCTTAA CAGTAATTGC CATCCTGATT GTCCTTGTGG TTGTGGTACG

1201 AAAATTACCT TCTGCCGATC ATAGCACAAG GGTTCAGCAA ATGGGCTAAG
     TTTTAATGGA AGACGGCTAG TATCGTGTTC CCAAGTCGTT TACCCGATTC
```

-continued

```
1251  GAGCGCAAGG ATGATCTTGA TAACGAGAAA ATGCTGGGTA CTAGAGAACG
      CTCGCGTTCC TACTAGAACT ATTGCTCTTT TACGACCCAT GATCTCTTGC

1301  CAAGCTTACG TATGGCTGCT TGTGGGCGTT TCGCACTAAG AAAGTACATT
      GTTCGAATGC ATACCGACGA ACACCCGCAA AGCGTGATTC TTTCATGTAA

1351  CGTTTTATCG CCCACCTGGA ACGCAGACCA TCGTAAAAGT CCCAGCCTCT
      GCAAAATAGC GGGTGGACCT TGCGTCTGGT AGCATTTTCA GGGTCGGAGA

1401  TTTAGCGCTT TTCCCATGTC GTCCGTATGG ACGACCTCTT TGCCCATGTC
      AAATCGCGAA AAGGGTACAG CAGGCATACC TGCTGGAGAA ACGGGTACAG

1451  GCTGAGGCAG AAATTGAAAC TGGCATTGCA ACCAAAGAAG GAGGAAAAAC
      CGACTCCGTC TTTAACTTTG ACCGTAACGT TGGTTTCTTC CTCCTTTTTG

1501  TGCTGCAGGT CTCGGAGGAA TTAGTCATGG AGGCCAAGGC TGCTTTTGAG
      ACGACGTCCA GAGCCTCCTT AATCAGTACC TCCGGTTCCG ACGAAAACTC

1551  GATGCTCAGG AGGAAGCCAG AGCGGAGAAG CTCCGAGAAG CACTTCCACC
      CTACGAGTCC TCCTTCGGTC TCGCCTCTTC GAGGCTCTTC GTGAAGGTGG

1601  ATTAGTGGCA GACAAAGGCA TCGAGGCAGC CGCAGAAGTT GTCTGCGAAG
      TAATCACCGT CTGTTTCCGT AGCTCCGTCG GCGTCTTCAA CAGACGCTTC

1651  TGGAGGGGCT CCAGGCGGAC ATCGGAGCAG CATTAGTTGA AACCCCGCGC
      ACCTCCCCGA GGTCCGCCTG TAGCCTCGTC GTAATCAACT TTGGGGCGCG

1701  GGTCACGTAA GGATAATACC TCAAGCAAAT GACCGTATGA TCGGACAGTA
      CCAGTGCATT CCTATTATGG AGTTCGTTTA CTGGCATACT AGCCTGTCAT

1751  TATCGTTGTC TCGCCAAACT CTGTGCTGAA GAATGCCAAA CTCGCACCAG
      ATAGCAACAG AGCGGTTTGA GACACGACTT CTTACGGTTT GAGCGTGGTC

1801  CGCACCCGCT AGCAGATCAG GTTAAGATCA TAACACACTC CGGAAGATCA
      GCGTGGGCGA TCGTCTAGTC CAATTCTAGT ATTGTGTGAG GCCTTCTAGT

1851  GGAAGGTACG CGGTCGAACC ATACGACGCT AAAGTACTGA TGCCAGCAGG
      CCTTCCATGC GCCAGCTTGG TATGCTGCGA TTTCATGACT ACGGTCGTCC

1901  AGGTGCCGTA CCATGGCCAG AATTCCTAGC ACTGAGTGAG AGCGCCACGT
      TCCACGGCAT GGTACCGGTC TTAAGGATCG TGACTCACTC TCGCGGTGCA

1951  TAGTGTACAA CGAAAGAGAG TTTGTGAACC GCAAACTATA CCACATTGCC
      ATCACATGTT GCTTTCTCTC AAACACTTGG CGTTTGATAT GGTGTAACGG

2001  ATGCATGGCC CCGCCAAGAA TACAGAAGAG GAGCAGTACA AGGTTACAAA
      TACGTACCGG GGCGGTTCTT ATGTCTTCTC CTCGTCATGT TCCAATGTTT

2051  GGCAGAGCTT GCAGAAACAG AGTACGTGTT TGACGTGGAC AAGAAGCGTT
      CCGTCTCGAA CGTCTTTGTC TCATGCACAA ACTGCACCTG TTCTTCGCAA

2101  GCGTTAAGAA GGAAGAAGCC TCAGGTCTGG TCCTCTCGGG AGAACTGACC
      CGCAATTCTT CCTTCTTCGG AGTCCAGACC AGGAGAGCCC TCTTGACTGG

2151  AACCCTCCCT ATCATGAGCT AGCTCTGGAG GGACTGAAGA CCCGACCTGC
      TTGGGAGGGA TAGTACTCGA TCGAGACCTC CCTGACTTCT GGGCTGGACG

2201  GGTCCCGTAC AAGGTCGAAA CAATAGGAGT GATAGGCACA CCGGGGTCGG
      CCAGGGCATG TTCCAGCTTT GTTATCCTCA CTATCCGTGT GGCCCCAGCC

2251  GCAAGTCAGC TATTATCAAG TCAACTGTCA CGGCACGAGA TCTTGTTACC
      CGTTCAGTCG ATAATAGTTC AGTTGACAGT GCCGTGCTCT AGAACAATGG

2301  AGCGGAAAGA AAGAAAATTG TCGCGAAATT GAGGCCGACG TGCTAAGACT
      TCGCCTTTCT TTCTTTTAAC AGCGCTTTAA CTCCGGCTGC ACGATTCTGA

2351  GAGGGGTATG CAGATTACGT CGAAGACAGT AGATTCGGTT ATGCTCAACG
      CTCCCCATAC GTCTAATGCA GCTTCTGTCA TCTAAGCCAA TACGAGTTGC

2401  GATGCCACAA AGCCGTAGAA GTGCTGTACG TTGACGAAGC GTTCGCGTGC
      CTACGGTGTT TCGGCATCTT CACGACATGC AACTGCTTCG CAAGCGCACG

2451  CACGCAGGAG CACTACTTGC CTTGATTGCT ATCGTCAGGC CCCGCAAGAA
      GTGCGTCCTC GTGATGAACG GAACTAACGA TAGCAGTCCG GGCGTTCTT

2501  GGTAGTACTA TGCGGAGACC CCATGCAATG CGGATTCTTC AACATGATGC
      CCATCATGAT ACGCCTCTGG GGTACGTTAC GCCTAAGAAG TTGTACTACG

2551  AACTAAAGGT ACATTTCAAT CACCCTGAAA AGACATATG CACCAAGACA
      TTGATTTCCA TGTAAAGTTA GTGGGACTTT TTCTGTATAC GTGGTTCTGT
```

-continued

```
2601  TTCTACAAGT ATATCTCCCG GCGTTGCACA CAGCCAGTTA CAGCTATTGT
      AAGATGTTCA TATAGAGGGC CGCAACGTGT GTCGGTCAAT GTCGATAACA

2651  ATCGACACTG CATTACGATG GAAAGATGAA AACCACGAAC CCGTGCAAGA
      TAGCTGTGAC GTAATGCTAC CTTTCTACTT TTGGTGCTTG GGCACGTTCT

2701  AGAACATTGA AATCGATATT ACAGGGGCCA CAAAGCCGAA GCCAGGGGAT
      TCTTGTAACT TTAGCTATAA TGTCCCCGGT GTTTCGGCTT CGGTCCCCTA

2751  ATCATCCTGA CATGTTTCCG CGGGTGGGTT AAGCAATTGC AAATCGACTA
      TAGTAGGACT GTACAAAGGC GCCCACCCAA TTCGTTAACG TTTAGCTGAT

2801  TCCCGGACAT GAAGTAATGA CAGCCGCGGC CTCACAAGGG CTAACCAGAA
      AGGGCCTGTA CTTCATTACT GTCGGCGCCG GAGTGTTCCC GATTGGTCTT

2851  AAGGAGTGTA TGCCGTCCGG CAAAAAGTCA ATGAAAACCC ACTGTACGCG
      TTCCTCACAT ACGGCAGGCC GTTTTTCAGT TACTTTTGGG TGACATGCGC

2901  ATcACATCAG AGCATGTGAA CGTGTTGCTC ACCCGCACTG AGGACAGGCT
      TAGTGTAGTC TCGTACACTT GCACAACGAG TGGGCGTGAC TCCTGTCCGA

2951  AGTGTGGAAA ACCTTGCAGG GCGACCCATG GATTAAGCAG CTCACTAACA
      TCACACCTTT TGGAACGTCC CGCTGGGTAC CTAATTCGTC GAGTGATTGT

3001  TACCTAAAGG AAACTTTCAG GCTACTATAG AGGACTGGGA AGCTGAACAC
      ATGGATTTCC TTTGAAAGTC CGATGATATC TCCTGACCCT TCGACTTGTG

3051  AAGGGAATAA TTGCTGCAAT AAACAGCCCC ACTCCCCGTG CCAATCCGTT
      TTCCCTTATT AACGACGTTA TTTGTCGGGG TGAGGGGCAC GGTTAGGCAA

3101  CAGCTGCAAG ACCAACGTTT GCTGGGCGAA AGCATTGGAA CCGATACTAG
      GTCGACGTTC TGGTTGCAAA CGACCCGCTT TCGTAACCTT GGCTATGATC

3151  CCACGGCCGG TATCGTACTT ACCGGTTGCC AGTGGAGCGA ACTGTTCCCA
      GGTGCCGGCC ATAGCATGAA TGGCCAACGG TCACCTCGCT TGACAAGGGT

3201  CAGTTTGCGG ATGACAAACC ACATTCGGCC ATTTACGCCT TAGACGTAAT
      GTCAAACGCC TACTGTTTGG TGTAAGCCGG TAAATGCGGA ATCTGCATTA

3251  TTGCATTAAG TTTTTCGGCA TGGACTTGAC AAGCGGACTG TTTTCTAAAC
      AACGTAATTC AAAAAGCCGT ACCTGAACTG TTCGCCTGAC AAAAGATTTG

3301  AGAGCATCCC ACTAACGTAC CATCCCGCCG ATTCAGCGAG GCCGGTAGCT
      TCTCGTAGGG TGATTGCATG GTAGGGCGGC TAAGTCGCTC CGGCCATCGA

3351  CATTGGGACA ACAGCCCAGG AACCCGCAAG TATGGGTACG ATCACGCCAT
      GTAACCCTGT TGTCGGGTCC TTGGGCGTTC ATACCCATGC TAGTGCGGTA

3401  TGCCGCCGAA CTCTCCCGTA GATTTCCGGT GTTCCAGCTA GCTGGGAAGG
      ACGGCGGCTT GAGAGGGCAT CTAAAGGCCA CAAGGTCGAT CGACCCTTCC

3451  GCACACAACT TGATTTGCAG ACGGGGAGAA CCAGAGTTAT CTCTGCACAG
      CGTGTGTTGA ACTAAACGTC TGCCCCTCTT GGTCTCAATA GAGACGTGTC

3501  CATAACCTGG TCCCGGTGAA CCGCAATCTT CCTCACGCCT TAGTCCCCGA
      GTATTGGACC AGGGCCACTT GGCGTTAGAA GGAGTGCGGA ATCAGGGGCT

3551  GTACAAGGAG AAGCAACCCG GCCCGGTCGA AAAATTCTTG AACCAGTTCA
      CATGTTCCTC TTCGTTGGGC CGGGCCAGCT TTTTAAGAAC TTGGTCAAGT

3601  AACACCACTC AGTACTTGTG GTATCAGAGG AAAAAATTGA AGCTCCCCGT
      TTGTGGTGAG TCATGAACAC CATAGTCTCC TTTTTTAACT TCGAGGGGCA

3651  AAGAGAATCG AATGGATCGC CCCGATTGGC ATAGCCGGTG CAGATAAGAA
      TTCTCTTAGC TTACCTAGCG GGGCTAACCG TATCGGCCAC GTCTATTCTT

3701  CTACAACCTG GCTTTCGGGT TTCCGCCGCA GGCACGGTAC GACCTGGTGT
      GATGTTGGAC CGAAAGCCCA AAGGCGGCGT CCGTGCCATG CTGGACCACA

3751  TCATCAACAT TGGAACTAAA TACAGAAACC ACCACTTTCA GCAGTGCGAA
      AGTAGTTGTA ACCTTGATTT ATGTCTTTGG TGGTGAAAGT CGTCACGCTT

3801  GACCATGCGG CGACCTTAAA AACCCTTTCG CGTTCGGCCC TGAATTGCCT
      CTGGTACGCC GCTGGAATTT TTGGGAAAGC GCAAGCCGGG ACTTAACGGA

3851  TAACCCAGOA GGCACCCTCG TGGTGAAGTC CTATGGCTAC GCCGACCGCA
      ATTGGGTCCT CCGTGGGAGC ACCACTTCAG GATACCGATG CGGCTGGCGT

3901  ACAGTGAGGA CGTAGTCACC GCTCTTGCCA GAAAGTTTGT CAGGGTGTCT
      TGTCACTCCT GCATCAGTGG CGAGAACGGT CTTTCAAACA GTCCCACAGA
```

```
3951  GCAGCGAGAC CAGATTGTGT CTCAAGCAAT ACAGAAATGT ACCTGATTTT
      CGTCGCTCTG GTCTAACACA GAGTTCGTTA TGTCTTTACA TGGACTAAAA

4001  CCGACAACTA GACAACAGCC GTACACGGCA ATTCACCCCG CACCATCTGA
      GGCTGTTGAT CTGTTGTCGG CATGTGCCGT TAAGTGGGGC GTGGTAGACT

4051  ATTGCGTGAT TTCGTCCGTG TATGAGGGTA CAAGAGATGG AGTTGGAGCC
      TAACGCACTA AAGCAGGCAC ATACTCCCAT GTTCTCTACC TCAACCTCGG

4101  GCGCCGTCAT ACCGCACCAA AAGGGAGAAT ATTGCTGACT GTCAAGAGGA
      CGCGGCAGTA TGGCGTGGTT TTCCCTCTTA TAACGACTGA CAGTTCTCCT

4151  AGCAGTTGTC AACGCAGCCA ATCCGCTGGG TAGACCAGGC GAAGGAGTCT
      TCGTCAACAG TTGCGTCGGT TAGGCGACCC ATCTGGTCCG CTTCCTCAGA

4201  GCCGTGCCAT CTATAAACGT TGGCCGACCA GTTTTACCGA TTCAGCCACG
      CGGCACGGTA GATATTTGCA ACCGGCTGGT CAAAATGGCT AAGTCGGTGC

4251  GAGACAGGCA CCGCAAGAAT GACTGTGTGC CTAGGAAAGA AAGTGATCCA
      CTCTGTCCGT GGCGTTCTTA CTGACACACG GATCCTTTCT TTCACTAGGT

4301  CGCGGTCGGC CCTGATTTCC GGAAGCACCC AGAAGCAGAA GCCTTGAAAT
      GCGCCAGCCG GGACTAAAGG CCTTCGTGGG TCTTCGTCTT CGGAACTTTA

4351  TGCTACAAAA CGCCTACCAT GCAGTGGCAG ACTTAGTAAA TGAACATAAC
      ACGATGTTTT GCGGATGGTA CGTCACCGTC TGAATCATTT ACTTGTATTG

4401  ATCAAGTCTG TCGCCATTCC ACTGCTATCT ACAGGCATTT ACGCAGCCGG
      TAGTTCAGAC AGCGGTAAGG TGACGATAGA TGTCCGTAAA TGCGTCGGCC

4451  AAAAGACCGC CTTGAAGTAT CACTTAACTG CTTGACAACC GCGCTAGACA
      TTTTCTGGCG GAACTTCATA GTGAATTGAC GAACTGTTGG CGCGATCTGT

4501  GAACTGACGC GGACGTAACC ATCTATTGCC TGGATAAGAA GTGGAAGGAA
      CTTGACTGCG CCTGCATTGG TAGATAACGG ACCTATTCTT CACCTTCCTT

4551  AGAATCGACG CGGCACTCCA ACTTAAGGAG TCTGTAACAG AGCTGAAGGA
      TCTTAGCTGC GCCGTGAGGT TGAATTCCTC AGACATTGTC TCGACTTCCT

4601  TGAAGATATG GAGATCGACG ATGAGTTAGT ATGGATCCAT CCAGACAGTT
      ACTTCTATAC CTCTAGCTGC TACTCAATCA TACCTAGGTA GGTCTGTCAA

4651  GCTTGAAGGG AAGAAAGGGA TTCAGTACTA CAAAAGGAAA ATTGTATTCG
      CGAACTTCCC TTCTTTCCCT AAGTCATGAT GTTTTCCTTT TAACATAAGC

4701  TACTTCGAAG GCACCAAATT CCATCAAGCA GCAAAAGACA TGGCGGAGAT
      ATGAAGCTTC CGTGGTTTAA GGTAGTTCGT CGTTTTCTGT ACCGCCTCTA

4751  AAAGGTCCTG TTCCCTAATG ACCAGGAAAG TAATGAACAA CTGTGTGCCT
      TTTCCAGGAC AAGGGATTAC TGGTCCTTTC ATTACTTGTT GACACACGGA

4801  ACATATTGGG TGAGACCATG GAAGCAATCC GCGAAAAGTG CCCGGTCGAC
      TGTATAACCC ACTCTGGTAC CTTCGTTAGG CGCTTTTCAC GGGCCAGCTG

4851  CATAACCCGT CGTCTAGCCC GCCCAAAACG TTGCCGTGCC TTTGCATGTA
      GTATTGGGCA GCAGATCGGG CGGGTTTTGC AACGGCACGG AAACGTACAT

4901  TGCCATGACG CCAGAAAGGG TCCACAGACT TAGAAGCAAT AACGTCAAAG
      ACGGTACTGC GGTCTTTCCC AGGTGTCTGA ATCTTCGTTA TTGCAGTTTC

4951  AAGTTACAGT ATGCTCCTCC ACCCCCTTC CTAAGCACAA AATTAAGAAT
      TTCAATGTCA TACGAGGAGG TGGGGGAAG GATTCGTGTT TTAATTCTTA

5001  GTTCAGAAGG TTCAGTGCAC GAAAGTAGTC CTGTTTAATC CGCACACTCC
      CAAGTCTTCC AAGTCACGTG CTTTCATCAG GACAAATTAG GCGTGTGAGG

5051  CGCATTCGTT CCCGCCCGTA AGTACATAGA AGTGCCAGAA CAGCCTACCG
      GCGTAAGCAA GGGCGGGCAT TCATGTATCT TCACGGTCTT GTCGGATGGC

5101  CTCCTCCTGC ACAGGCCGAG GAGGCCCCCC AAGTTGTAGC GACACCGTCA
      GAGGAGGACG TGTCCGGCTC CTCCGGGGGC TTCAACATCG CTGTGGCAGT

5151  CCATCTACAG CTGATAACAC CTGCTTGAT GTCACAGACA TCTCACTGGA
      GGTAGATGTC GACTATTGTG GAGCGAACTA CAGTGTCTGT AGAGTGACCT

5201  TATGGATGAC AGTAGCGAAG GCTCACTTTT TTCGAGCTTT AGCGGATCGG
      ATACCTACTG TCATCGCTTC CGAGTGAAAA AAGCTCGAAA TCGCCTAGCC

5251  ACAACTCTAT TACTAGTGCC TCGTACCCCG GCCATCAACA CGCGTCTGCG
      TGTTGAGATA ATGATCACGG AGCATGGGGC CGGTAGTTGT GCGCAGACGC
```

```
5301  TTCGACCAGG CTGCGCGTTC TCGCGGCCAT AGCAACCGAC GTACGGCGTT
      AAGCTGGTCC GACGCGCAAG AGCGCCGGTA TCGTTGGCTG CATGCCGCAA

5351  GCGCCCTCGC CGGCAGCAAG AAGCCACGGA AGTCCGCCCG GAGCAGAAAA
      CGCGGGAGCG GCCGTCGTTC TTCGGTGCCT TCAGGCGGGC CTCGTCTTTT

5401  TGCCCACGCT ACTGCGGGTT TATATAGACG GTCCCCACGG GATGGGGAAA
      ACGGGTGCGA TGACGCCCAA ATATATCTGC CAGGGGTGCC CTACCCCTTT

5451  ACCACCACCA CGCAACTGCT GGTGGCCCTG GGTTCGCGCG ACGATATCGT
      TGGTGGTGGT GCGTTGACGA CCACCGGGAC CCAAGCGCGC TGCTATAGCA

5501  CTACGTACCC GAGCCGATGA CTTACTGGCG GGTGCTGGGG GCTTCCGAGA
      GATGCATGGG CTCGGCTACT GAATGACCGC CCACGACCCC CGAAGGCTCT

5551  CAATCGCGAA CATCTACACC ACACAACACC GCCTCGACCA GGGTGAGATA
      GTTAGCGCTT GTAGATGTGG TGTGTTGTGG CGGAGCTGGT CCCACTCTAT

5601  TCGGCCGGGG ACGCGGCGGT GGTAATGACA AGCGCCCAGA TAACAATGGG
      AGCCGGCCCC TGCGCCGCCA CCATTACTGT TCGCGGGTCT ATTGTTACCC

5651  CATGCCTTAT GCCGTGACCG ACGCCGTTCT GGCTCCTCAT ATCGGGGGGG
      GTACGGAATA CGGCACTGGC TGCGGCAAGA CCGAGGAGTA TAGCCCCCCC

5701  AGGCTGGGAG CTCACATGCC CCGCCCCCGG CCCTCACCCT CATCTTCGAC
      TCCGACCCTC GAGTGTACGG GGCGGGGGCC GGGAGTGGGA GTAGAAGCTG

5751  CGCCATCCCA TCGCCGCCCT CCTGTGCTAC CCGGCCGCGC GGTACCTTAT
      GCGGTAGGGT AGCGGCGGGA GGACACGATG GGCCGGCGCG CCATGGAATA

5801  GGGCAGCATG ACCCCCCAGG CCGTGCTGGC GTTCGTGGCC CTCATCCCGC
      CCCGTCGTAC TGGGGGGTCC GGCACGACCG CAAGCACCGG GAGTAGGGCG

5851  CGACCTTGCC CGGCACCAACATCGTGCTTG GGGCCCTTCC GGAGGACAGA
      GCTGGAACGG GCCGTGGTTG TAGCACGAAC CCCGGGAAGG CCTCCTGTCT

5901  CACATCGACC GCCTGGCCAA ACGCCAGCGC CCCGGCGAGC GGCTGGACCT
      GTGTAGCTGG CGGACCGGTT TGCGGTCGCG GGGCCGCTCG CCGACCTGGA

5951  GGCTATGCTG GCTGCGATTC GCCGCGTTTA CGGGCTACTT GCCAATACGG
      CCGATACGAC CGACGCTAAG CGGCGCAAAT GCCCGATGAA CGGTTATGCC

6001  TGCGGTATCT GCAGTGCGGC GGGTCGTGGC GGGAGGACTG GGGACAGCTT
      ACGCCATAGA CGTCACGCCG CCCAGCACCG CCCTCCTGAC CCCTGTCGAA

6051  TCGGGGACGG CCGTGCCGCC CCAGGGTGCC GAGCCCCAGA GCAACGCGGG
      AGCCCCTGCC GGCACGGCGG GGTCCCACGG CTCGGGGTCT CGTTGCGCCC

6101  CCCACGACCC CATATCGGGG ACACGTTATT TACCCTGTTT CGGGCCCCCG
      GGGTGCTGGG GTATAGCCCC TGTGCAATAA ATGGGACAAA GCCCGGGGGC

6151  AGTTGCTGGC CCCCAACGGC GACCTGTATA ACGTGTTTGC CTGGGCCTTG
      TCAACGACCG GGGGTTGCCG CTGGACATAT TGCACAAACG GACCCGGAAC

6201  GACGTCTTGG CCAAACGCCT CCGTTCCATG CACGTCTTTA TCCTGGATTA
      CTGCAGAACC GGTTTGCGGA GGCAAGGTAC GTGCAGAAAT AGGACCTAAT

6251  CGACCAATCG CCCGCCGGCT GCCGGGACGC CCTGCTGCAA CTTACCTCCG
      GCTGGTTAGC GGGCGGCCGA CGGCCCTGCG GACGACGTT GAATGGAGGC

6301  GGATGGTCCA GACCCACGTC ACCACCCCCG GCTCCATACC GACGATATGC
      CCTACCAGGT CTGGGTGCAG TGGTGGGGGC CGAGGTATGG CTGCTATACG

6351  GACCTGGCGC GCACGTTTGC CCGGGAGATG GGGGAGGCTA ACACTAGTAT
      CTGGACCGCG CGTGCAAACG GGCCCTCTAC CCCCTCCGAT TGTGATCATA

6401  GGACAGTTGG TCGTCAGGAC CTAGTTCACT AGAGATAGTA GACCGAAGGC
      CCTGTCAACC AGCAGTCCTG GATCAAGTGA TCTCTATCAT CTGGCTTCCG

6451  AGGTGGTGGT GGCTGACGTT CATGCCGTCC AAGAGCCTGC CCCTATTCCA
      TCCACCACCA CCGACTGCAA GTACGGCAGG TTCTCGGACG GGATAAGGT

6501  CCGCCAAGGC TAAAGAAGAT GGCCCGCCTG GCAGCGGCAA GAAAAGAGCC
      GGCGGTTCCG ATTTCTTCTA CCGGGCGGAC CGTCGCCGTT CTTTTCTCGG

6551  CACTCCACCG GCAAGCAATA GCTCTGAGTC CCTCCACCTC TCTTTTGGTG
      GTGAGGTGGC CGTTCGTTAT CGAGACTCAG GGAGGTGGAG AGAAAACCAC

6601  GGGTATCCAT GTCCCTCGGA TCAATTTTCG ACGGAGAGAC GGCCCGCCAG
      CCCATAGGTA CAGGGAGCCT AGTTAAAAGC TGCCTCTCTG CCGGGCGGTC
```

```
6651  GCAGCGGTAC AACCCCTGGC AACAGGCCCC ACGGATGTGC CTATGTCTTT
      CGTCGCCATG TTGGGGACCG TTGTCCGGGG TGCCTACACG GATACAGAAA

6701  CGGATCGTTT TCCGACGGAG AGATTGATGA GCTGAGCCGC AGAGTAACTG
      GCCTAGCAAA AGGCTGCCTC TCTAACTACT CGACTCGGCG TCTCATTGAC

6751  AGTCCGAACC CGTCCTGTTT GGATCATTTG AACCGGGCGA AGTGAACTCA
      TCAGGCTTGG GCAGGACAAA CCTAGTAAAC TTGGCCCGCT TCACTTGAGT

6801  ATTATATCGT CCCGATCAGC CGTATCTTTT CCACTACGCA AGCAGAGACG
      TAATATAGCA GGGCTAGTCG GCATAGAAAA GGTGATGCGT TCGTCTCTGC

6851  TAGACGCAGG AGCAGGAGGA CTGAATACTG ACTAACCGGG GTAGGTGGGT
      ATCTGCGTCC TCGTCCTCCT GACTTATGAC TGATTGGCCC CATCCACCCA

6901  ACATATTTTC GACGGACACA GGCCCTGGGC ACTTGCAAAA GAAGTCCGTT
      TGTATAAAAG CTGCCTGTGT CCGGGACCCG TGAACGTTTT CTTCAGGCAA

6951  CTGCAGAACC AGCTTACAGA ACCGACCTTG GAGCGCAATG TCCTGGAAAG
      GACGTCTTGG TCGAATGTCT TGGCTGGAAC CTCGCGTTAC AGGACCTTTC

7001  AATTCATGCC CCGGTGCTCG ACACGTCGAA AGAGGAACAA CTCAAACTCA
      TTAAGTACGG GGCCACGAGC TGTGCAGCTT TCTCCTTGTT GAGTTTGAGT

7051  GGTACCAGAT GATGCCCACC GAAGCCAACA AAAGTAGGTA CCAGTCTCGT
      CCATGGTCTA CTACGGGTGG CTTCGGTTGT TTTCATCCAT GGTCAGAGCA

7101  AAAGTAGAAA ATCAGAAAGC CATAACCACT GAGCGACTAC TGTCAGGACT
      TTTCATCTTT TAGTCTTTCG GTATTGGTGA CTCGCTGATG ACAGTCCTGA

7151  ACGACTGTAT AACTCTGCCA CAGATCAGCC AGAATGCTAT AAGATCACCT
      TGCTGACATA TTGAGACGGT GTCTAGTCGG TCTTACGATA TTCTAGTGGA

7201  ATCCGAAACC ATTGTACTCC AGTAGCGTAC CGGCGAACTA CTCCGATCCA
      TAGGCTTTGG TAACATGAGG TCATCGCATG GCCGCTTGAT GAGGCTAGGT

7251  CAGTTCGCTG TAGCTGTCTG TAACAACTAT CTGCATGAGA ACTATCCGAC
      GTCAAGCGAC ATCGACAGAC ATTGTTGATA GACGTACTCT TGATAGGCTG

7301  AGTAGCATCT TATCAGATTA CTGACGAGTA CCATGCTTAC TTGGATATGG
      TCATCGTAGA ATAGTCTAAT GACTGCTCAT GCTACGAATG AACCTATACC

7351  TAGACGGGAC AGTCGCCTGC CTGGATACTG CAACCTTCTG CCCCGCTAAG
      ATCTGCCCTG TCAGCGGACG GACCTATGAC GTTGGAAGAC GGGGCGATTC

7401  CTTAGAAGTT ACCCGAAAAA ACATGAGTAT AGAGCCCCGA ATATCCGCAG
      GAATCTTCAA TGGGCTTTTT TGTACTCATA TCTCGGGGCT TATAGGCGTC

7451  TGCGGTTCCA TCAGCGATGC AGAACACGCT ACAAAATGTG CTCATTGCCG
      ACGCCAAGGT AGTCGCTACG TCTTGTGCGA TGTTTTACAC GAGTAACGGC

7501  CAACTAAAAG AAATTGCAAC GTCACGCAGA TGCGTGAACT GCCAACACTG
      GTTGATTTTC TTTAACGTTG CAGTGCGTCT ACGCACTTGA CGGTTGTGAC

7551  GACTCAGCGA CATTCAATGT CGAATGCTTT CGAAAATATG CATGTAATGA
      CTGAGTCGCT GTAAGTTACA GCTTACGAAA GCTTTTATAC GTACATTACT

7601  CGAGTATTGG GAGGAGTTCG CTCGGAAGCC AATTAGGATT ACCACTGAGT
      GCTCATAACC CTCCTCAAGC GAGCCTTCGG TTAATCCTAA TGGTGACTCA

7651  TTGTCACCGC ATATGTAGCT AGACTGAAAG GCCCTAAGGC CGCCGCACTA
      AACAGTGGCG TATACATCGA TCTGACTTTC CGGGATTCCG GCGGCGTGAT

7701  TTTGCAAAGA CGTATAATTT GGTCCCATTG CAAGAAGTGC CTATGGATAG
      AAACGTTTCT GCATATTAAA CCAGGGTAAC GTTCTTCACG GATACCTATC

7751  ATTCGTCATG GACATGAAAA GAGACGTGAA AGTTACACCA GGCACGAAAC
      TAAGCAGTAC CTGTACTTTT CTCTGCACTT TCAATGTGGT CCGTGCTTTG

7801  ACACAGAAGA AAGACCGAAA GTACAAGTGA TACAAGCCGC AGAACCCCTG
      TGTGTCTTCT TTCTGGCTTT CATGTTCACT ATGTTCGGCG TCTTGGGGAC

7851  GCGACTGCTT ACTTATGCGG GATTCACCGG GAATTAGTGC GTAGGCTTAC
      CGCTGACGAA TGAATACGCC CTAAGTGGCC CTTAATACG CATCCGAATG

7901  GGCCGTCTTG CTTCCAAACA TTCACACGCT TTTTGACATG TCGGCGGAGG
      CCGGCAGAAC GAAGGTTTGT AAGTGTGCGA AAAACTGTAC AGCCGCCTCC

7951  ATTTTGATGC AATCATAGCA GAAACACTTCA AGCAAGGCGA CCCGGTACTG
      TAAAACTACG TTAGTATCGT CTTGTGAAGT TCGTTCCGCT GGGCCATGAC
```

-continued

```
8001  GAGACGGATA TCGCATGATT CGACAAAAGC CAAGACGACG CTATGGCGTT
      CTCTGCCTAT AGCGTAGTAA GCTGTTTTCG GTTCTGCTGC GATACCGCAA

8051  AACCGGTCTG ATGATCTTGG AGGACCTGGG TGTGGATCAA CCACTACTCG
      TTGGCCAGAC TACTAGAACC TCCTGGACCC ACACCTAGTT GGTGATGAGC

8101  ACTTGATCGA GTGCGCCTTT GGAGAAATAT CATCCACCCA TCTACCTACG
      TGAACTAGCT CACGCGGAAA CCTCTTTATA GTAGGTGGGT AGATGGATGC

8151  GGTACTCGTT TTAAATTCGG GGCGATGATG AAATCCGGAA TGTTCCTCAC
      CCATGAGCAA AATTTAAGCC CCGCTACTAC TTTAGGCCTT ACAAGGAGTG

8201  ACTTTTTGTC AACACAGTTT TGAATGTCGT TATCGCCAGC AGAGTACTAG
      TGAAAAACAG TTGTGTCAAA ACTTACAGCA ATAGCGGTCG TCTCATGATC

8251  AAGAGCGGCT TAAAACGTCC AGATGTGCAG CGTTCATTGG CGACGACAAC
      TTCTCGCCGA ATTTTGCAGG TCTACACGTC GCAAGTAACC GCTGCTGTTG

8301  ATCATACATG GAGTAGTATC TGACAAAGAA ATGGCTGAGA GGTGCGCCAC
      TAGTATGTAC CTCATCATAG ACTGTTTCTT TACCGACTCT CCACGCGGTG

8351  CTGGCTCAAC ATGGAGGTTA AGATCATCGA CGCAGTCATC GGTGAGAGAC
      GACCGAGTTG TACCTCCAAT TCTAGTAGCT GCGTCAGTAG CCACTCTCTG

8401  CACCTTACTT CTGCGGCGGA TTTATCTTGC AAGATTCGGT TACTTCCACA
      GTGGAATGAA GACGCCGCCT AAATAGAACG TTCTAAGCCA ATGAAGGTGT

8451  GCGTGCCGCG TGGCGGACCC CCTGAAAAGG CTGTTTAAGT TGGGTAAACC
      CGCACGGCGC ACCGCCTGGG GGACTTTTCC GACAAATTCA ACCCATTTGG

8501  GCTCCCAGCC GACGACGAGC AAGACGAAGA CAGAAGACGC GCTCTGCTAG
      CGAGGGTCGG CTGCTGCTCG TTCTGCTTCT GTCTTCTGCG CGAGACGATC

8551  ATGAAACAAA GGCGTGGTTT AGAGTAGGTA TAACAGGCAC TTTAGCAGTG
      TACTTTGTTT CCGCACCAAA TCTCATCCAT ATTGTCCGTG AAATCGTCAC

8601  GCCGTGACGA CCCGGTATGA GGTAGACAAT ATTACACCTG TCCTACTGGC
      CGGCACTGCT GGGCCATACT CCATCTGTTA TAATGTGGAC AGGATGACCG

8651  ATTGAGAACT TTTGCCCAGA GCAAAAGAGC ATTCCAAGCC ATCAGAGGGG
      TAACTCTTGA AAACGGGTCT CGTTTTCTCG TAAGGTTCGG TAGTCTCCCC

8701  AAATAAAGCA TCTCTACGGT GGTCCTAAAT AGTCAGCATA GTACATTTCA
      TTTATTTCGT AGAGATGCCA CCAGGATTTA TCAGTCGTAT CATGTAAAGT

8751  TCTGACTAAT ACTACAACAC CACCACCTCT AGCCCGGGCT CGAGATCTGC
      AGACTGATTA TGATGTTGTG GTGGTGGAGA TCGGGCCCGA GCTCTAGACG

8801  GATCTAAGTA AGCTTGGCAT TCCGGTACTG TTGGTAAAGC CACCATGGAA
      CTAGATTCAT TCGAACCGTA AGGCCATGAC AACCATTTCG GTGGTACCTT

8851  GACGCCAAAA ACATAAAGAA AGGCCCGGCG CCATTCTATC CGCTGGAAGA
      CTGCGGTTTT TGTATTTCTT TCCGGGCCGC GGTAAGATAG GCGACCTTCT

8901  TGGAACCGCT GGAGAGCAAC TGCATAAGGC TATGAAGAGA TACGCCCTGG
      ACCTTGGCGA CCTCTCGTTG ACGTATTCCG ATACTTCTCT ATGCGGGACC

8951  TTCCTGGAAC AATTGCTTTT ACAGATGCAC ATATCGAGGT GGACATCACT
      AAGGACCTTG TTAACGAAAA TGTCTACGTG TATAGCTCCA CCTGTAGTGA

9001  TACGCTGAGT ACTTCGAAAT GTCCGTTCGG TTGGCAGAAG CTATGAAACG
      ATGCGACTCA TGAAGCTTTA CAGGCAAGCC AACCGTCTTC GATACTTTGC

9051  ATATGGGCTG AATACAAATC ACAGAATCGT CGTATGCAGT GAAAACTCTC
      TATACCCGAC TTATGTTTAG TGTCTTAGCA GCATACGTCA CTTTTGAGAG

9101  TTCAATTCTT TATGCCGGTG TTGGGCGCGT TATTTATCGG AGTTGCAGTT
      AAGTTAAGAA ATACGGCCAC AACCCGCGCA ATAAATAGCC TCAACGTCAA

9151  GCGCCCGCGA ACGACATTTA TAATGAACGT GAATTGCTCA ACAGTATGGG
      CGCGGGCGCT TGCTGTAAAT ATTACTTGCA CTTAACGAGT TGTCATACCC

9201  CATTTCGCAG CCTACCGTGG TGTTCGTTTC CAAAAGGGGT TGCAAAAAA
      GTAAAGCGTC GGATGGCACC ACAAGCAAAG GTTTTTCCCC AACGTTTTTT

9251  TTTTGAACGT GCAAAAAAAG CTCCCAATCA TCCAAAAAAT TATTATCATG
      AAAACTTGCA CGTTTTTTTC GAGGGTTAGT AGGTTTTTTA ATAATAGTAC

9301  GATTCTAAAA CGGATTACCA GCGATTTCAG TCGATGTACA CGTTCGTCAC
      CTAAGATTTT GCCTAATGGT CCCTAAAGTC AGCTACATGT GCAAGCAGTG
```

```
9351  ATCTCATCTA CCTCCCGGTT TTAATGAATA CGATTTTGTG CCAGAGTCCT
      TAGAGTAGAT GGAGGGCCAA AATTACTTAT GCTAAAACAC GGTCTCAGGA

9401  TCGATAGGGA CAAGACAATT GCACTGATCA TGAACTCCTC TGGATCTACT
      AGCTATCCCT GTTCTGTTAA CGTGACTAGT ACTTGAGGAG ACCTAGATGA

9451  GGTCTGCCTA AAGGTGTCGC TCTGCCTCAT AGAACTGCCT GCGTGAGATT
      CCAGACGGAT TTCCACAGCG AGACGGAGTA TCTTGACGGA CGCACTCTAA

9501  CTCGCATGCC AGAGATCCTA TTTTTGGCAA TCAAATCATT CCGGATACTG
      GAGCGTACGG TCTCTAGGAT AAAAACCGTT AGTTTAGTAA GGCCTATGAC

9551  CGATTTTAAG TGTTGTTCCA TTCCATCACG GTTTTGGAAT GTTTACTACA
      GCTAAAATTC ACAACAAGGT AAGGTAGTGC CAAAACCTTA CAAATGATGT

9601  CTCGGATATT TGATATGTGG ATTTCGAGTC GTCTTAATGT ATAGATTTGA
      GAGCCTATAA ACTATACACC TAAAGCTCAG CAGAATTACA TATCTAAACT

9651  AGAAGAGCTG TTTCTGAGGA GCCTTCAGGA TTACAAGATT CAAAGTGCGC
      TCTTCTCGAC AAAGACTCCT CGGAAGTCCT AATGTTCTAA GTTTCACGCG

9701  TGCTGGTGCC AACCCTATTC TCCTTCTTCG CCAAAAGCAC TCTGATTGAC
      ACGACCACGG TTGGGATAAG AGGAAGAAGC GGTTTTCGTG AGACTAACTG

9751  AAATACGATT TATCTAATTT ACACGAAATT GCTTCTGGTG GCGCTCCCCT
      TTTATGCTAA ATAGATTAAA TGTGCTTTAA CGAAGACCAC CGCGAGGGGA

9801  CTCTAAGGAA GTCGGGGAAG CGGTTGCCAA GAGGTTCCAT CTGCCAGGTA
      GAGATTCCTT CAGCCCCTTC GCCAACGGTT CTCCAAGGTA GACGGTCCAT

9851  TCAGGCAAGG ATATGGGCTC ACTGAGACTA CATCAGCTAT TCTGATTACA
      AGTCCGTTCC TATACCCGAG TGACTCTGAT GTAGTCGATA AGACTAATGT

9901  CCCGAGGGGG ATGATAAACC GGGCGCGGTC GGTAAAGTTG TTCCATTTTT
      GGGCTCCCCC TACTATTTGG CCCGCGCCAG CCATTTCAAC AAGGTAAAAA

9951  TGAAGCGAAG GTTGTCGATC TGGATACCGC GAAAACGCTG GGCGTTAATC
      ACTTCGCTTC CAACACCTAG ACCTATGGCC CTTTTGCGAC CCGCAATTAG

10001 AAAGAGGCGA ACTGTGTGTG AGAGGTCCTA TGATTATGTC CGGTTATGTA
      TTTCTCCGCT TGACACACAC TCTCCAGGAT ACTAATACAG GCCAATACAT

10051 AACAATCCGG AAGCGACCAA CGCCTTGATT GACAAGGATG GATGGCTACA
      TTGTTAGGCC TTCGCTGGTT GCGGAACTAA CTGTTCCTAC CTACCGATGT

10101 TTCTGGAGAC ATAGCTTACT GGGACGAAGA CGAACACTTC TTCATCGTTG
      AAGACCTCTG TATCGAATGA CCCTGCTTCT GCTTGTGAAG AAGTAGCAAC

10151 ACCGCCTGAA GTCTCTGATT AAGTACAAAG GCTATCAGGT GGCTCCCGCT
      TGGCGGACTT CAGAGACTAA TTCATGTTTC CGATAGTCCA CCGAGGGCGA

10201 GAATTGGAAT CCATCTTGCT CCAACACCCC AACATCTTCG ACGCAGGTGT
      CTTAACCTTA GGTAGAACGA GGTTGTGGGG TTGTAGAAGC TGCGTCCACA

10251 CGCAGGTCTT CCCGACGATG ACGCCGGTGA ACTTCCCGCC GCCGTTGTTG
      GCGTCCAGAA GGGCTGCTAC TGCGGCCACT TGAAGGGCGG CGGCAACAAC

10301 TTTTGGAGCA CGGAAAGACG ATGACGGAAA AAGAGATCGT GGATTACGTC
      AAAACCTCGT GCCTTTCTGC TACTGCCTTT TTCTCTAGCA CCTAATGCAG

10351 GCCAGTCAAG TAACAACCGC GAAAAAGTTG CGCGGAGGAG TTGTGTTTGT
      CGGTCAGTTC ATTGTTGGCG CTTTTTCAAC GCGCCTCCTC AACACAAACA

10401 GGACGAAGTA CCGAAAGGTC TTACCGGAAA ACTCGACGCA AGAAAAATCA
      CCTGCTTCAT GGCTTTCCAG AATGGCCTTT TGAGCTGCGT TCTTTTTAGT

10451 GAGAGATCCT CATAAAGGCC AAGAAGGGCG GAAAGATCGC CGTGTAATTC
      CTCTCTAGGA GTATTTCCGG TTCTTCCCGC CTTTCTAGCG GCACATTAAG

10501 TAGAGGCGCG CCGATCTCAC GATCCCCTGA AAAGGCTGTT TAAGTTGGGT
      ATCTCCGCGC GGCTAGAGTG CTAGGGGACT TTTCCGACAA ATTCAACCCA

10551 AAACCGCTCC CAGCCGACGA CGAGCAAGAC GAAGACAGAA GACGCGCTCT
      TTTGGCGAGG GTCGGCTGCT GCTCGTTCTG CTTCTGTCTT CTGCGCGAGA

10601 GCTAGATGAA ACAAAGGCGT GGTTTAGAGT AGGTATAACA GGCACTTTAG
      CGATCTACTT TGTTTCCGCA CCAAATCTCA TCCATATTGT CCGTGAAATC

10651 CAGTGGCCGT GACGACCCGG TATGAGGTAG ACAATATTAC ACCTGTCCTA
      GTCACCGGCA CTGCTGGGCC ATACTCCATC TGTTATAATG TGGACAGGAT
```

```
10701  CTGGCATTGA GAACTTTTGC CCAGAGCAAA AGAGCATTCC AAGCCATCAG
       GACCGTAACT CTTGAAAACG GGTCTCGTTT TCTCGTAAGG TTCGGTAGTC

10751  AGGGGAAATA AAGCATCTCT ACGGTGGTCC TAAATAGTCA GCATAGTACA
       TCCCCTTTAT TTCGTAGAGA TGCCACCAGG ATTTATCAGT CGTATCATGT

10801  TTTCATCTGA CTAATACTAC AACACCACCA CCATGAATAG AGGATTCTTT
       AAAGTAGACT GATTATGATG TTGTGGTGGT GGTACTTATC TCCTAAGAAA

10851  AACATGCTCG GCCGCCGCCC CTTCCCGGCC CCCACTGCCA TGTGGAGGCC
       TTGTACGAGC CGGCGGCGGG GAAGGGCCGG GGGTGACGGT ACACCTCCGG

10901  GCGGAGAAGG AGGCAGGCGG CCCCGATGCC TGCCCGCAAC GGGCTGGCTT
       CGCCTCTTCC TCCGTCCGCC GGGGCTACGG ACGGGCGTTG CCCGACCGAA

10951  CTCAAATCCA GCAACTGACC ACAGCCGTCA GTGCCCTAGT CATTGGACAG
       GAGTTTAGGT CGTTGACTGG TGTCGGCAGT CACGGGATCA GTAACCTGTC

11001  GCAACTAGAC CTCAACCCCC ACGTCCACGC CAGCCACCGC GCCAGAAGAA
       CGTTGATCTG GAGTTGGGGG TGCAGGTGCG GTCGGTGGCG CGGTCTTCTT

11051  GCAGGCGCCC AAGCAACCAC CGAAGCCGAA GAAACCAAAA ACGCAGGAGA
       CGTCCGCGGG TTCGTTGGTG GCTTCGGCTT CTTTGGTTTT TGCGTCCTCT

11101  AGAAGAAGAA GCAACCTGCA AAACCCAAAC CCGGAAAGAG ACAGCGCATG
       TCTTCTTCTT CGTTGGACGT TTTGGGTTTG GGCCTTTCTC TGTCGCGTAC

11151  GCACTTAAGT TGGAGGCCGA CAGATTGTTC GACGTCAAGA ACGAGGACGG
       CGTGAATTCA ACCTCCGGCT GTCTAACAAG CTGCAGTTCT TGCTCCTGCC

11201  AGATGTCATC GGGCACGCAC TGGCCATGGA AGGAAAGGTA ATGAAACCTC
       TCTACAGTAG CCCGTGCGTG ACCGGTACCT TCCTTTCCAT TACTTTGGAG

11251  TGCACGTGAA AGGAACCATC GACCACCCTG TGCTATCAAA GCTCAAATTT
       ACGTGCACTT TCCTTGGTAG CTGGTGGGAC ACGATAGTTT CGAGTTTAAA

11301  ACCAAGTCGT CAGCATACGA CATGGAGTTC GCACAGTTGC CAGTCAACAT
       TGGTTCAGcA GTCGTATGCT GTACCTCAAG CGTGTCAACG GTCAGTTGTA

11351  GAGAAGTGAG GCATTCACCT ACACCAGTGA ACACCCCGAA GGATTCTATA
       CTCTTCACTC CGTAAGTGGA TGTGGTCACT TGTGGGGCTT CCTAAGATAT

11401  ACTGGCACCA CGGAGCGGTG CAGTATAGTG GAGGTAGATT TACCATCCCT
       TGACCGTGGT GCCTCGCCAC GTCATATCAC CTCCATCTAA ATGGTAGGGA

11451  CGCGGAGTAG GAGGCAGAGG AGACAGCGGT CGTCCGATCA TGGATAACTC
       GCGCCTCATC CTCCGTCTCC TCTGTCGCCA GCAGGCTAGT ACCTATTGAG

11501  CGGTCGGGTT GTCGCGATAG TCCTCGGTGG AGCTGATCAA GGAACACGAA
       GCCAGCCCAA CAGCGCTATC AGGAGCCACC TCGACTACTT CCTTGTGCTT

11551  CTGCCCTTTC GGTCGTCACC TGGAATAGTA AAGGGAAGAC AATTAAGACG
       GACGGGAAAG CCAGCAGTGG ACCTTATCAT TTCCCTTCTG TTAATTCTGC

11601  ACCCCGGAAG GGACAGAAGA GTGGTCCGCA GCACCACTGG TCACGGCAAT
       TGGGGCCTTC CCTGTCTTCT CACCAGGCGT CGTGGTGACC AGTGCCGTTA

11651  GTGTTTGCTC GGAAATGTGA GCTTCCCATG CGACCGCCCG CCCACATGCT
       CACAAACGAG CCTTTACACT CGAAGGGTAC GCTGGCGGGC GGGTGTACGA

11701  ATACCCGCGA ACCTTCCAGA GCCCTCGACA TCCTTGAAGA GAACGTGAAC
       TATGGGCGCT TGGAAGGTCT CGGGAGCTGT AGGAACTTCT CTTGCACTTG

11751  CATGAGGCCT ACGATACCCT GCTCAATGCC ATATTGCGGT GCGGATCGTC
       GTACTCCGGA TGCTATGGGA CGAGTTACGG TATAACGCCA CGCCTAGCAG

11801  TGGCAGAAGC AAAAGAAGCG TCATCGATGA CTTTACCCTG ACCAGCCCCT
       ACCGTCTTCG TTTTCTTCGC AGTAGCTACT GAAATGGGAC TGGTCGGGA

11851  ACTTGGGCAC ATGCTCGTAC TGCCACCATA CTGAACCGTG CTTCAGCCCT
       TGAACCCGTG TACGAGCATG ACGGTGGTAT GACTTGGCAC GAAGTCGGGA

11901  GTTAAGATCG AGCAGGTCTG GGACGAAGCG GACGATAACA CCATACGCAT
       CAATTCTAGC TCGTCCAGAC CCTGCTTCGC CTGCTATTGT GGTATGCGTA

11951  ACAGACTTCC GCCCAGTTTG GATACGACCA AAGCGGAGCA GCAAGCGCAA
       TGTCTGAAGG CGGGTCAAAC CTATGCTGGT TTCGCCTCGT CGTTCGCGTT

12001  ACAAGTACCG CTACATGTCG CTTAAGCAGG ATCACACCGT TAAAGAAGGC
       TGTTCATGGC CATGTACAGC GAATTCGTCC TAGTGTGGCA ATTTCTTCCG
```

```
12051  ACCATGGATG ACATCAAGAT TAGGACCTCA GGACCGTGTA GAAGGCTTAG
       TGGTACCTAC TGTAGTTCTA ATCGTGGAGT CCTGGCACAT CTTCCGAATC

12101  CTACAAAGGA TACTTTCTCC TCGCAAAATG CCCTCCAGGG GACAGCGTAA
       GATGTTTCCT ATGAAAGAGG AGCGTTTTAC GGGAGGTCCC CTGTCGCATT

12151  CGGTTAGCAT AGTGAGTAGC AACTCAGCAA CGTCATGTAC ACTGGCCCGC
       GCCAATCGTA TCACTCATCG TTGAGTCGTT GCAGTACATG TGACCGGGCG

12201  AAGATAAAAC CAAAATTCGT GGGACGGGAA AAATATGATC TACCTCCCGT
       TTCTATTTTG GTTTTAAGCA CCCTGCCCTT TTTATACTAG ATGGAGGGCA

12251  TCACGGTAAA AAAATTCCTT GCACAGTGTA CGACCGTCTG AAAGAAACAA
       AGTGCCATTT TTTTAAGGAA CGTGTCACAT GCTGGCAGAC TTTCTTTGTT

12301  CTGCAGGCTA CATCACTATG CACAGGCCGG GCCCGCACGC TTATACATCC
       GACGTCCGAT GTAGTGATAC GTGTCCGGCC CGGGCGTGCG AATATGTAGG

12351  TACCTGGAAG AATCATCAGG GAAAGTTTAC GCAAAGCCGC CATCTGGGAA
       ATGGACCTTC TTAGTAGTCC CTTTCAAATG CGTTTCGGCG GTAGACCCTT

12401  GAACATTACG TATGAGTGCA AGTGCGGCGA CTACAAGACC GGAACCGTTT
       CTTGTAATGC ATACTCACGT TCACGCCGCT GATGTTCTGG CCTTGGCAAA

12451  CGACCCGCAC CGAAATCACT GGTTGCACCG CCATCAAGCA GTGCGTCGCC
       GCTGGGCGTG GCTTTAGTGA CCAACGTGGC GGTAGTTCGT CACGCAGCGG 12 501 TATAAGAGCG ACCAAACGAA GTGGGTCTTC AACTCACCGG ACTTGATCCG
       ATATTCTCGC TGGTTTGCTT CACCCAGAAG TTGAGTGGCC TGAACTAGGC

12551  ACATGACGAC CACACGGTCC AAGGGAAATT GCATTTGCCT TTCAAGTTGA
       TGTACTGCTG GTGTGCCAGG TTCCCTTTAA CGTAAACGGA AAGTTCAACT

12601  TCCCGAGTAC CTGCATGGTC CCTGTTGCCC ACGCGCCGAA TGTAATACAT
       AGGGCTCATG GACGTACCAG GGACAACGGG TGCGCGGCTT ACATTATGTA

12651  GGCTTTAAAC ACATCAGCCT CCAATTAGAT ACAGACCACT TGACATTGCT
       CCGAAATTTG TGTAGTCGGA GGTTAATCTA TGTCTGGTGA ACTGTAACGA

12701  CACCACCAGO AGACTAGGGG CAAACCCGGA ACCAACCACT GAATGGATCG
       GTGGTGGTCC TCTGATCCCC GTTTGGGCCT TGGTTGGTGA CTTACCTAGC

12751  TCGGAAAGAC GGTCAGAAAC TTCACCGTCG ACCGAGATGG CCTGGAATAC
       AGCCTTTCTG CCAGTCTTTG AAGTGGCAGC TGGCTCTACC GGACCTTATG

12801  ATATGGGGAA ATCATGAGCC AGTGAGGGTC TATGCCCAAG AGTCAGCACC
       TATACCCCTT TAGTACTCGG TCACTCCCAG ATACGGGTTC TCAGTCGTGG

12851  AGGAGACCCT CACGGATGGC CACACGAAAT AGTACAGCAT TACTACCATC
       TCCTCTGGGA GTGCCTACCG GTGTGCTTTA TCATGTCGTA ATGATGGTAG

12901  GCCATCCTGT GTACACCATC TTAGCCGTCG CATCAGCTAC CGTGGCGATG
       CGGTAGGACA CATGTGGTAG AATCGGCAGC GTAGTCGATG GCACCGCTAC

12951  ATGATTGGCG TAACTGTTGC AGTGTTATGT GCCTGTAAAG CGCGCCGTGA
       TACTAACCGC ATTGACAACG TCACAATACA CGGACATTTC GCGCGGCACT

13001  GTGCCTGACG CCATACGCCC TGGCCCCAAA CGCCGTAATC CCAACTTCGC
       CACGGACTGC GGTATGCGGG ACCGGGGTTT GCGGCATTAG GGTTGAAGCG

13051  TGGCACTCTT GTGCTGCGTT AGGTCGGCCA ATGCTGAAAC GTTCACCGAG
       ACCGTGAGAA CACGACGCAA TCCAGCCGGT TACGACTTTG CAAGTGGCTC

13101  ACCATGAGTT ACTTGTGGTC GAACAGTCAG CCGTTCTTCT GGGTCCAGTT
       TGGTACTCAA TGAACACCAG CTTGTCAGTC GGCAAGAAGA CCCAGGTCAA

13151  GTGCATACCT TTGGCCGCTT TCATCGTTCT AATGCGCTGC TGCTCCTGCT
       CACGTATGGA AACCGGCGAA AGTAGCAAGA TTACGCGACG ACGAGGACGA

13201  GCCTGCCTTT TTTAGTGGTT GCCGGCGCCT ACCTGGCGAA GGTAGACGCC
       CGGACGGAAA AAATCACCAA CGGCCGCGGA TGGACCGCTT CCATCTGCGG

13251  TACGAACATG CGACCACTGT TCCAAATGTG CCACAGATAC CGTATAAGGC
       ATGCTTGTAC GCTGGTGACA AGGTTTACAC GGTGTCTATG GCATATTCCG

13301  ACTTGTTGAA AGGGCAGGGT ATGCCCCGCT CAATTTGGAG ATCACTGTCA
       TGAACAACTT TCCCGTCCCA TACGGGGCGA GTTAAACCTC TAGTGACAGT

13351  TGTCCTCGGA GGTTTTGCCT TCCACCAACC AAGAGTACAT TACCTGCAAA
       ACAGGAGCCT CCAAAACGGA AGGTGGTTGG TTCTCATGTA ATGGACGTTT
```

-continued

```
13401  TTCACCACTG TGGTCCCCTC CCCAAAAATC AAATGCTGCG GCTCCTTGGA
       AAGTGGTGAC ACCAGGGGAG GGGTTTTTAG TTTACGACGC CGAGGAACCT

13451  ATGTCAGCCG GCCGTTCATG CAGACTATAC CTGCAAGGTC TTCGGAGGGG
       TACAGTCGGC CGGCAAGTAC GTCTGATATG GACGTTCCAG AAGCCTCCCC

13501  TCTACCCCTT TATGTGGGGA GGAGCGCAAT GTTTTTGCGA CAGTGAGAAC
       AGATGGGGAA ATACACCCCT CCTCGCGTTA CAAAAACGCT GTCACTCTTG

13551  AGCCAGATGA GTGAGGCGTA CGTCGAACTG TCAGCAGATT GCGCGTCTGA
       TCGGTCTACT CACTCCGCAT GCAGCTTGAC AGTCGTCTAA CGCGCAGACT

13601  CCACGCGCAG GCGATTAAGG TGCACACTGC CGCGATGAAA GTAGGACTGC
       GGTGCGCGTC CGCTAATTCC ACGTGTGACG GCGCTACTTT CATCCTGACG

13651  GTATAGTGTA CGGGAACACT ACCAGTTTCC TAGATGTGTA CGTGAACGGA
       CATATCACAT GCCCTTGTGA TGGTCAAAGG ATCTACACAT GCACTTGCCT

13701  GTCACACCAG GAACGTCTAA AGACTTGAAA GTCATAGCTG GACCAATTTC
       CAGTGTGGTC CTTGCAGATT TCTGAACTTT CAGTATCGAC CTGGTTAAAG

13751  AGCATCGTTT ACGCCATTCG ATCATAAGGT CGTTATCCAT CGCGGCCTGG
       TCGTAGCAAA TGCGGTAAGC TAGTATTCCA GCAATAGGTA GCGCCGGACC

13801  TGTACAACTA TGACTTCCCG GAATATGGAG CGATGAAACC AGGAGCGTTT
       ACATGTTGAT ACTGAAGGGC CTTATACCTC GCTACTTTGG TCCTCGCAAA

13851  GGAGACATTC AAGCTACCTC CTTGACTAGC AAGGATCTCA TCGCCAGCAC
       CCTCTGTAAG TTCGATGGAG GAACTGATCG TTCCTAGAGT AGCGGTCGTG

13901  AGACATTAGG CTACTCAAGC CTTCCGCCAA GAACGTGCAT GTCCCGTACA
       TCTGTAATCC GATGAGTTCG GAAGGCGGTT CTTGCACGTA CAGGGCATGT

13951  CGCAGGCCGC ATCAGGATTT GAGATGTGGA AAAACAACTC AGGCCGCCCA
       GCGTCCGGCG TAGTCCTAAA CTCTACACCT TTTTGTTGAG TCCGGCGGGT

14001  CTGCAGGAAA CCGCACCTTT CGGGTGTAAG ATTGCAGTAA ATCCGCTCCG
       GACGTCCTTT GGCGTGGAAA GCCCACATTC TAACGTCATT TAGGCGAGGC

14051  AGCGGTGGAC TGTTCATACG GAACATTCC CATTTCTATT GACATCCCGA
       TCGCCACCTG ACAAGTATGC CCTTGTAAGG GTAAAGATAA CTGTAGGGCT

14101  ACGCTGCCTT TATCAGGACA TCAGATGCAC CACTGGTCTC AACAGTCAAA
       TGCGACGGAA ATAGTCCTGT AGTCTACGTG GTGACCAGAG TTGTCAGTTT

14151  TGTGAAGTCA GTGAGTGCAC TTATTCAGCA GACTTCGGCG GGATGGCCAC
       ACACTTCAGT CACTCACGTG AATAAGTCGT CTGAAGCCGC CCTACCGGTG

14201  CCTGCAGTAT GTATCCGACC GCGAAGGTCA ATGCCCCGTA CATTCGCATT
       GGACGTCATA CATAGGCTGG CGCTTCCAGT TACGGGGCAT GTAAGCCTAA

14251  CGAGCACAGC AACTCTCCAA GAGTCGACAG TACATGTCCT GGAGAAAGGA
       GCTCGTGTCG TTGAGAGGTT CTCAGCTGTC ATGTACAGGA CCTCTTTCCT

14301  GCGGTGACAG TACACTTTAG CACCGCGAGT CCACAGGCGA ACTTTATCGT
       CGCCACTGTC ATGTGAAATC GTGGCGCTCA GGTGTCCGCT TGAAATAGCA

14351  ATCGCTGTGT GGGAAGAAGA CAACATGCAA TGCAGAATGT AAACCACCAG
       TAGCGACACA CCCTTCTTCT GTTGTACGTT ACGTCTTACA TTTGGTGGTC

14401  CTGACCATAT CGTGAGCACC CCGCACAAAA ATGACCAAGA ATTTCAAGCC
       GACTGGTATA GCACTCGTGG GGCGTGTTTT TACTGGTTCT TAAAGTTCGG

14451  GCCATCTCAA AAACATCATG GAGTTGGCTG TTTGCCCTTT TCGGCGGCGC
       CGGTAGAGTT TTTGTAGTAC CTCAACCGAC AAACGGGAAA AGCCGCCGCG

14501  CTCGTCGCTA TTAATTATAG GACTTATGAT TTTTGCTTGC AGCATGATGC
       GAGCAGCGAT AATTAATATC CTGAATACTA AAAACGAACG TCGTACTACG

14551  TGACTAGCAC ACGAAGATGA CCGCTACGCC CCAATGATCC GACCAGCAAA
       ACTGATCGTG TGCTTCTACT GGCGATGCGG GGTTACTAGG CTGGTCGTTT

14601  ACTCGATGTA CTTCCGAGGA ACTGATGTGC ATAAGTGAGC ATGCGTTTAA
       TGAGCTACAT GAAGGCTCCT TGACTACACG TATTCACTCG TACGCAAATT

14651  ACTGGGCCCA ATGTTCCCCA ATGATCCGAC CAGCAAAACT CGATGTACTT
       TGACCCGGGT TACAAGGGGT TACTAGGCTG GTCGTTTTGA GCTACATGAA

14701  CCGAGGAACT GATGTGCATA ATGCATCAGG CTGGTACATT AGATCCCCGC
       GGCTCCTTGA CTACACGTAT TACGTAGTCC GACCATGTAA TCTAGGGGCG
```

```
14751  TTACCGCGGG CAATATAGCA ACACTAAAAA CTCGATGTAC TTCCGAGGAA
       AATGGCGCCC GTTATATCGT TGTGATTTTT GAGCTACATG AAGGCTCCTT

14801  GCGCAGTGCA TAATGCTGCG CAGTGTTGCC ACATAACCAC TATATTAACC
       CGCGTCACGT ATTACGACGC GTCACAACGG TGTATTGGTG ATATAATTGG

14851  ATTTATCTAG CGGACGCCAA AAACTCAATG TATTTCTGAG GAAGCGTGGT
       TAAATAGATC GCCTGCGGTT TTTGAGTTAC ATAAAGACTC CTTCGCACCA

14901  GCATAATGCC ACGCAGCGTC TGCATAACTT TTATTATTTC TTTTATTAAT
       CGTATTACGG TGCGTCGCAG ACGTATTGAA AATAATAAAG AAAATAATTA

14951  CAACAAAATT TTGTTTTTAA CATTTCAAAA AAAAAAAAAA AAAAAAAAA
       GTTGTTTTAA AACAAAAATT GTAAAGTTTT TTTTTTTTT TTTTTTTTT

15001  AAAATTTAAA TTAATTAAGC GGCCGCCTCG AGGACGTCAG
       TTTTTTTTTT TTTTAAATTT AATTAATTCG CCGGCGGAGC TCCTGCAGTC

15051  GTGGCACTTT TCGGGGAAAT GTGCGCGGAA CCCCTATTTG TTTATTTTTC
       CACCGTGAAA AGCCCCTTTA CACGCGCCTT GGGGATAAAC AAATAAAAAG

15101  TAAATACATT CAAATATGTA TCCGCTCATG AGACAATAAC CCTGATAAAT
       ATTTATGTAA GTTTATACAT AGGCGAGTAC TCTGTTATTG GGACTATTTA

15151  GCTTCAATAA TATTGAAAAA GGAAGAGTAT GAGTATTCAA CATTTCCGTG
       CGAAGTTATT ATAACTTTTT CCTTCTCATA CTCATAAGTT GTAAAGGCAC

15201  TCGCCCTTAT TCCCTTTTTT GCGGCATTTT GCCTTCCTGT TTTTGCTCAC
       AGCGGGAATA AGGGAAAAAA CGCCGTAAAA CGGAAGGACA AAAACGAGTG

15251  CCAGAAACGC TGGTGAAAGT AAAAGATGCT GAAGATCAGT TGGGTGCACG
       GGTCTTTGCG ACCACTTTCA TTTTCTACGA CTTCTAGTCA ACCCACGTGC

15301  AGTGGGTTAC ATCGAACTGG ATCTCAACAG CGGTAAGATC CTTGAGAGTT
       TCACCCAATG TAGCTTGACC TAGAGTTGTC GCCATTCTAG GAACTCTCAA

15351  TTCGCCCCGA AGAACGTTTT CCAATGATGA GCACTTTTAA AGTTCTGCTA
       AAGCGGGGCT TCTTGCAAAA GGTTACTACT CGTGAAAATT TCAAGACGAT

15401  TGTGGCGCGG TATTATCCCG TATTGACGCC GGGCAAGAGC AACTCGGTCG
       ACACCGCGCC ATAATAGGGC ATAACTGCGG CCCGTTCTCG TTGAOCCAGC

15451  CCGCATACAC TATTCTCAGA ATGACTTGGT TGAGTACTCA CCAGTCACAG
       GGCGTATGTG ATAAGAGTCT TACTGAACCA ACTCATGAGT GGTCAGTGTC

15501  AAAAGCATCT TACGGATGGC ATGACAGTAA GAGAATTATG CAGTGCTGCC
       TTTTCGTAGA ATGCCTACCG TACTGTCATT CTCTTAATAC GTCACGACGG

15551  ATAACCATGA GTGATAACAC TGCGGCCAAC TTACTTCTGA CAACGATCGG
       TATTGGTACT CACTATTGTG ACGCCGGTTG AATGAAGACT GTTGCTAGCC

15601  AGGACCGAAG GAGCTAACCG CTTTTTTGCA CAACATGGGG GATCATGTAA
       TCCTGGCTTC CTCGATTGGC GAAAAAACGT GTTGTACCCC CTAGTACATT

15651  CTCGCCTTGA TCGTTGGGAA CCGGAGCTGA ATGAAGCCAT ACCAAACGAC
       GAGCGGAACT AGCAACCCTT GGCCTCGACT TACTTCGGTA TGGTTTGCTG

15701  GAGCGTGACA CCACGATGCC TGTAGCAATG GCAACAACGT TGCGCAAACT
       CTCGCACTGT GGTGCTACGG ACATCGTTAC CGTTGTTGCA ACGCGTTTGA

15751  ATTAACTGGC GAACTACTTA CTCTAGCTTC CCGGCAACAA TTAATAGACT
       TAATTGACCG CTTGATGAAT GAGATCGAAG GGCCGTTGTT AATTATCTGA

15801  GGATGGAGGC GGATAAAGTT GCAGGACCAC TTCTGCGCTC GGCCCTTCCG
       CCTACCTCCG CCTATTTCAA CGTCCTGGTG AAGACGCGAG CCGGGAAGGC

15851  GCTGGCTGGT TTATTGCTGA TAAATCTGGA GCCGGTGAGC GTGGGTCTCG
       CGACCGACCA AATAACGACT ATTTAGACCT CGGCCACTCG CACCCAGAGC

15901  CGGTATCATT GCAGCACTGG GGCCAGATGG TAAGCCCTCC CGTATCGTAG
       GCCATAGTAA CGTCGTGACC CCGGTCTACC ATTCGGGAGG GCATAGCATC

15951  TTATCTACAC GACGGGGAGT CAGGCAACTA TGGATGAACG AAATAGACAG
       AATAGATGTG CTGCCCCTCA GTCCGTTGAT ACCTACTTGC TTTATCTGTC

16001  ATCGCTGAGA TAGGTGCCTC ACTGATTAAG CATTGGTAAC TGTCAGACCA
       TAGCGACTCT ATCCACGGAG TGACTAATTC GTAACCATTG ACAGTCTGGT

16051  AGTTTACTCA TATATACTTT AGATTGATTT AAAACTTCAT TTTTAATTTA
       TCAAATGAGT ATATATGAAA TCTAACTAAA TTTTGAAGTA AAAATTAAAT
```

```
16101  AAAGGATCTA GGTGAAGATC CTTTTTGATA ATCTCATGAC CAAAATCCCT
       TTTCCTAGAT CCACTTCTAG GAAAAACTAT TAGAGTACTG GTTTTAGGGA

16151  TAACGTGAGT TTTCGTTCCA CTGAGCGTCA GACCCCGTAG AAAAGATCAA
       ATTGCACTCA AAAGCAAGGT GACTCGCAGT CTGGGGCATC TTTTCTAGTT

16201  AGGATCTTCT TGAGATCCTT TTTTTCTGCG CGTAATCTGC TGCTTGCAAA
       TCCTAGAAGA ACTCTAGGAA AAAAAGACGC GCATTAGACG ACGAACGTTT

16251  CAAAAAAACC ACCGCTACCA GCGGTGGTTT GTTTGCCGGA TCAAGAGCTA
       GTTTTTTTGG TGGCGATGGT CGCCACCAAA CAAACGGCCT AGTTCTCGAT

16301  CCAACTCTTT TTCCGAAGGT AACTGGCTTC AGCAGAGCGC AGATACCAAA
       GGTTGAGAAA AAGGCTTCCA TTGACCGAAG TCGTCTCGCG TCTATGGTTT

16351  TACTGGTCTT CTAGTGTAGC CGTAGTTAGG CCACCACTTC AAGAACTCTG
       ATGACCAGAA GATCACATCG GCATCAATCC GGTGGTGAAG TTCTTGAGAC

16401  TAGCACCGCC TACATACCTC GCTCTGCTAA TCCTGTTACC AGTGGCTGCT
       ATCGTGGCGG ATGTATGGAG CGAGACGATT AGGACAATGG TCACCGACGA

16451  GCCAGTGGCG ATAAGTCGTG TCTTACCGGG TTGGACTCAA GACGATAGTT
       CGGTCACCGC TATTCAGCAC AGAATGGCCC AACCTGAGTT CTGCTATCAA

16501  ACCGGATAAG GCGCAGCGGT CGGGCTGAAC GGGGGGTTCG TGCACACAGC
       TGGCCTATTC CGCGTCGCCA GCCCGACTTG CCCCCCAAGC ACGTGTGTCG

16551  CCAGCTTGGA GCGAACGACC TACACCGAAC TGAGATACCT ACAGCGTGAG
       GGTCGAACCT CGCTTGCTGG ATGTGGCTTG ACTCTATGGA TGTCGCACTC

16601  CTATGAGAAA GCGCCACGCT TCCCGAAGGG AGAAAGGCGG ACAGGTATCC
       GATACTCTTT CGCGGTGCGA AGGGCTTCCC TCTTTCCGCC TGTCCATAGG

16651  GGTAAGCGGC AGGGTCGGAA CAGGAGAGCG CACGAGGGAG CTTCCAGGGG
       CCATTCGCCG TCCCAGCCTT GTCCTCTCGC GTGCTCCCTC GAAGGTCCCC

16701  GAAACGCCTG GTATCTTTAT AGTCCTGTCG GGTTTCGCCA CCTCTGACTT
       CTTTGCGGAC CATAGAAATA TCAGGACACC CCAAAGCGGT GGAGACTGAA

16751  GAGCGTCGAT TTTTGTGATG CTCGTCAGGG GGGCGGAGCC TATGGAAAAA
       CTCGCAGCTA AAAACACTAC GAGCAGTCCC CCCGCCTCGG ATACCTTTTT

16801  CGCCAGCAAC GCGGCCTTTT TACGGTTCCT GGCCTTTTGC TGGCCTTTTG
       GCGGTCGTTG CGCCGGAAAA ATGCCAAGGA CCGGAAAACG ACCGGAAAAC

16851  CTCACATGTG GGAGGCTAGA GTACATTTAG GTGACACTAT AGAA
       GAGTGTACAC CCTCCGATCT CATGTAAATC CACTGTGATA TCTT
```

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. A method for treating a mammal harboring a solid tumor which expresses higher levels of High Affinity Laminin Receptors (LAMR) than normal cells of the same lineage comprising intraperitoneally administering to a mammal in need of such treatment a therapeutically effective amount of a Replication Competent (RC) Sindbis virus vector and a therapeutically effective amount of a prodrug, wherein said vector encodes a suicide gene, and wherein said RC Sindbis virus vector is a RC mut-4 vector comprising SEQ. ID NOS.: 2-8 and said administration causes reduction in size of said tumor.

2. The method of claim 1 wherein said suicide gene is the Herpes virus thymidine kinase gene.

3. The method of claim 1 wherein said suicide gene is the Vericella zoster Virus thymidine kinase gene.

4. The method of claim 1, wherein said suicide gene is the cytosine deaminase gene.

5. The method of claim 2 wherein said prodrug is ganciclovir.

6. The method of claim 2 wherein said prodrug is 5-fluorocytosine.

7. The method of claim 2 wherein said prodrug is acyclovir.

8. The method of claim 2 wherein said prodrug is FIAU.

9. A method for treating a mammal harboring a solid tumor which expresses higher levels of High Affinity Laminin Receptors (LAMR) than normal cells of the same lineage comprising parenterally administering to a mammal in need of such treatment a therapeutically effective amount of a Replication Competent (RC) Sindbis virus vector, wherein said vector encodes a suicide gene and, wherein said RC Sindbis virus vector is a RC mut-4 vector comprising SEQ. ID NOS.: 2-8, and said administration causes a reduction in tumor size.

10. The method of claim 9 further comprising administering an effective amount of a pro drug.

11. The method of claim 9 wherein said suicide gene is the Herpes virus thymidine kinase gene.

12. The method of claim 10 wherein said prodrug is ganciclovir.

* * * * *

SEQUENCE LISTING

```
<160> NUMBER OF SEQ ID NOS: 8

<210> SEQ ID NO 1
<211> LENGTH: 16894
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
attgacggcg tagtacacac tattgaatca aacagccgac caattgcact accatcacaa      60
tggagaagcc agtagtaaac gtagacgtag accccccagag tccgtttgtc gtgcaactgc    120
```

```
aaaaaagctt cccgcaattt gaggtagtag cacagcaggt cactccaaat gaccatgcta    180
atgccagagc attttcgcat ctggccagta aactaatcga gctggaggtt cctaccacag    240
cgacgatctt ggacataggc agcgcaccgg ctcgtagaat gttttccgag caccagtatc    300
attgtgtctg ccccatgcgt agtccagaag acccggaccg catgatgaaa tatgccagta    360
aactggcgga aaaagcgtgc aagattacaa acaagaactt gcatgagaag attaaggatc    420
tccggaccgt acttgatacg ccggatgctg aaacaccatc gctctgcttt cacaacgatg    480
ttacctgcaa catgcgtgcc gaatattccg tcatgcagga cgtgtatatc aacgctcccg    540
gaactatcta tcatcaggct atgaaaggcg tgcggaccct gtactggatt ggcttcgaca    600
ccacccagtt catgttctcg gctatggcag gttcgtaccc tgcgtacaac accaactggg    660
ccgacgagaa agtccttgaa gcgcgtaaca tcggactttg cagcacaaag ctgagtgaag    720
gtaggacagg aaaattgtcg ataatgagga agaaggagtt gaagcccggg tcgcgggttt    780
atttctccgt aggatcgaca ctttatccag aacacagagc cagcttgcag agctggcatc    840
ttccatcggt gttccacttg aatggaaagc agtcgtacac ttgccgctgt gatacagtgg    900
tgagttgcga aggctacgta gtgaagaaaa tcaccatcag tcccgggatc acgggagaaa    960
ccgtgggata cgcggttaca cacaatagcg agggcttctt gctatgcaaa gttactgaca   1020
cagtaaaagg agaacgggta tcgttccctg tgtgcacgta catcccggcc accatatgcg   1080
atcagatgac tggtataatg gccacggata tatcacctga cgatgcacaa aaacttctgg   1140
ttgggctcaa ccagcgaatt gtcattaacg gtaggactaa caggaacacc aacaccatgc   1200
aaaattacct tctgccgatc atagcacaag ggttcagcaa atgggctaag gagcgcaagg   1260
atgatcttga taacgagaaa atgctgggta ctagagaacg caagcttacg tatggctgct   1320
tgtgggcgtt tcgcactaag aaagtacatt cgttttatcg cccacctgga acgcagacca   1380
tcgtaaaagt cccagcctct tttagcgctt ttcccatgtc gtccgtatgg acgacctctt   1440
tgcccatgtc gctgaggcag aaattgaaac tggcattgca accaaagaag gaggaaaaac   1500
tgctgcaggt ctcggaggaa ttagtcatgg aggccaaggc tgcttttgag gatgctcagg   1560
aggaagccag agcggagaag ctccgagaag cacttccacc attagtggca gacaaaggca   1620
tcgaggcagc cgcagaagtt gtctgcgaag tggaggggct ccaggcggac atcggagcag   1680
cattagttga aacccgcgcg ggtcacgtaa ggataatacc tcaagcaaat gaccgtatga   1740
tcggacagta tatcgttgtc tcgccaaact ctgtgctgaa gaatgccaaa ctcgcaccag   1800
cgcacccgct agcagatcag gttaagatca taacacactc cggaagatca ggaaggtacg   1860
cggtcgaacc atacgacgct aaagtactga tgccagcagg aggtgccgta ccatggccag   1920
aattcctagc actgagtgag agcgccacgt tagtgtacaa cgaaagagag tttgtgaacc   1980
gcaaactata ccacattgcc atgcatggcc ccgccaagaa tacagaagag gagcagtaca   2040
aggttacaaa ggcagagctt gcagaaacag agtacgtgtt tgacgtggac aagaagcgtt   2100
gcgttaagaa ggaagaagcc tcaggtctgg tcctctcggg agaactgacc aaccctccct   2160
atcatgagct agctctggag ggactgaaga cccgacctgc ggtcccgtac aaggtcgaaa   2220
caataggagt gataggcaca ccggggtcgg gcaagtcagc tattatcaag tcaactgtca   2280
cggcacgaga tcttgttacc agcggaaaga aagaaaattg tcgcgaaatt gaggccgacg   2340
tgctaagact gaggggtatg cagattacgt cgaagacagt agattcggtt atgctcaacg   2400
gatgccacaa agccgtagaa gtgctgtacg ttgacgaagc gttcgcgtgc cacgcaggag   2460
cactacttgc cttgattgct atcgtcaggc cccgcaagaa ggtagtacta tgcggagacc   2520
```

```
ccatgcaatg cggattcttc aacatgatgc aactaaaggt acatttcaat caccctgaaa    2580
aagacatatg caccaagaca ttctacaagt atatctcccg gcgttgcaca cagccagtta    2640
cagctattgt atcgacactg cattacgatg gaaagatgaa aaccacgaac ccgtgcaaga    2700
agaacattga aatcgatatt acaggggcca caaagccgaa gccaggggat atcatcctga    2760
catgtttccg cgggtgggtt aagcaattgc aaatcgacta tcccggacat gaagtaatga    2820
cagccgcggc ctcacaaggg ctaaccagaa aggagtgta  tgccgtccgg caaaaagtca    2880
atgaaaaccc actgtacgcg atcacatcag agcatgtgaa cgtgttgctc acccgcactg    2940
aggacaggct agtgtggaaa accttgcagg gcgacccatg gattaagcag ctcactaaca    3000
tacctaaagg aaactttcag gctactatag aggactggga agctgaacac aagggaataa    3060
ttgctgcaat aaacagcccc actccccgtg ccaatccgtt cagctgcaag accaacgttt    3120
gctgggcgaa agcattggaa ccgatactag ccacggccgg tatcgtactt accggttgcc    3180
agtggagcga actgttccca cagtttgcgg atgacaaacc acattcggcc atttacgcct    3240
tagacgtaat ttgcattaag ttttcggca  tggacttgac aagcggactg ttttctaaac    3300
agagcatccc actaacgtac catcccgccg attcagcgag gccggtagct cattgggaca    3360
acagcccagg aacccgcaag tatgggtacg atcacgccat tgccgccgaa ctctcccgta    3420
gatttccggt gttccagcta gctgggaagg gcacacaact tgatttgcag acggggagaa    3480
ccagagttat ctctgcacag cataacctgg tcccggtgaa ccgcaatctt cctcacgcct    3540
tagtccccga gtacaaggag aagcaacccg gcccggtcga aaaattcttg aaccagttca    3600
aacaccactc agtacttgtg gtatcagagg aaaaaattga agctccccgt aagagaatcg    3660
aatggatcgc cccgattggc atagccggtg cagataagaa ctacaacctg gctttcgggt    3720
ttccgccgca ggcacggtac gacctggtgt tcatcaacat tggaactaaa tacagaaacc    3780
accactttca gcagtgcgaa gaccatgcgg cgaccttaaa aaccctttcg cgttcggccc    3840
tgaattgcct taacccagga ggcaccctcg tggtgaagtc ctatggctac gccgaccgca    3900
acagtgagga cgtagtcacc gctcttgcca gaaagtttgt cagggtgtct gcagcgagac    3960
cagattgtgt ctcaagcaat acagaaatgt acctgatttt ccgacaacta gacaacagcc    4020
gtacacggca attcaccccg caccatctga attgcgtgat ttcgtccgtg tatgagggta    4080
caagagatgg agttggagcc gcgccgtcat accgcaccaa aagggagaat attgctgact    4140
gtcaagagga agcagttgtc aacgcagcca atccgctggg tagaccaggc gaaggagtct    4200
gccgtgccat ctataaacgt tggccgacca gttttaccga ttcagccacg gagacaggca    4260
ccgcaagaat gactgtgtgc ctaggaaaga agtgatcca  cgcggtcggc cctgatttcc    4320
ggaagcaccc agaagcagaa gccttgaaat tgctacaaaa cgcctaccat gcagtggcag    4380
acttagtaaa tgaacataac atcaagtctg tcgccattcc actgctatct acaggcattt    4440
acgcagccgg aaaagaccgc cttgaagtat cacttaactg cttgacaacc gcgctagaca    4500
gaactgacgc ggacgtaacc atctattgcc tggataagaa gtggaaggaa agaatcgacg    4560
cggcactcca acttaaggag tctgtaacag agctgaagga tgaagatatg gagatcgacg    4620
atgagttagt atggatccat ccagacagtt gcttgaaggg aagaaaggga ttcagtacta    4680
caaaaggaaa attgtattcg tacttcgaag gcaccaaatt ccatcaagca gcaaaagaca    4740
tggcggagat aaaggtcctg ttccctaatg accaggaaag taatgaacaa ctgtgtgcct    4800
acatattggg tgagaccatg gaagcaatcc gcgaaaagtg cccggtcgac cataacccgt    4860
cgtctagccc gcccaaaacg ttgccgtgcc tttgcatgta tgccatgacg ccagaaaggg    4920
```

```
tccacagact tagaagcaat aacgtcaaag aagttacagt atgctcctcc acccccttc    4980
ctaagcacaa aattaagaat gttcagaagg ttcagtgcac gaaagtagtc ctgtttaatc    5040
cgcacactcc cgcattcgtt cccgcccgta agtacataga agtgccagaa cagcctaccg    5100
ctcctcctgc acaggccgag gaggccccg aagttgtagc gacaccgtca ccatctacag    5160
ctgataacac ctcgcttgat gtcacagaca tctcactgga tatggatgac agtagcgaag    5220
gctcactttt ttcgagcttt agcggatcgg acaactctat tactagtgcc tcgtaccccg    5280
gccatcaaca cgcgtctgcg ttcgaccagg ctgcgcgttc tcgcggccat agcaaccgac    5340
gtacggcgtt gcgccctcgc cggcagcaag aagccacgga agtccgcccg gagcagaaaa    5400
tgcccacgct actgcgggtt tatatagacg gtccccacgg gatggggaaa accaccacca    5460
cgcaactgct ggtggccctg ggttcgcgcg acgatatcgt ctacgtaccc gagccgatga    5520
cttactggcg ggtgctgggg gcttccgaga caatcgcgaa catctacacc acacaacacc    5580
gcctcgacca gggtgagata tcggccgggg acgcggcggt ggtaatgaca agcgcccaga    5640
taacaatggg catgccttat gccgtgaccg acgccgttct ggctcctcat atcgggggg    5700
aggctgggag ctcacatgcc ccgccccgg ccctcaccct catcttcgac cgccatccca    5760
tcgccgccct cctgtgctac ccggccgcgc ggtaccttat gggcagcatg acccccagg    5820
ccgtgctggc gttcgtggcc ctcatcccgc cgaccttgcc cggcaccaac atcgtgcttg    5880
gggcccttcc ggaggacaga cacatcgacc gcctggccaa acgccagcgc cccggcgagc    5940
ggctggacct ggctatgctg gctgcgattc gccgcgttta cgggctactt gccaatacgg    6000
tgcggtatct gcagtgcggc gggtcgtggc gggaggactg gggacagctt tcggggacgg    6060
ccgtgccgcc ccagggtgcc gagccccaga gcaacgcggg cccacgaccc catatcgggg    6120
acacgttatt taccctgttt cgggcccccg agttgctggc cccaacggc gacctgtata    6180
acgtgtttgc ctgggccttg gacgtcttgg ccaaacgcct ccgttccatg cacgtcttta    6240
tcctggatta cgaccaatcg cccgccggct gccgggacgc cctgctgcaa cttacctccg    6300
ggatggtcca gacccacgtc accaccccg gctccatacc gacgatatgc gacctggcgc    6360
gcacgtttgc ccgggagatg ggggaggcta acactagtat ggacagttgg tcgtcaggac    6420
ctagttcact agagatagta gaccgaaggc aggtggtggt ggctgacgtt catgccgtcc    6480
aagagcctgc ccctattcca ccgccaaggc taaagaagat ggcccgcctg gcagcggcaa    6540
gaaaagagcc cactccaccg gcaagcaata gctctgagtc cctccacctc tcttttggtg    6600
gggtatccat gtccctcgga tcaattttcg acggagagac ggcccgccag gcagcggtac    6660
aacccctggc aacaggcccc acggatgtgc ctatgtcttt cggatcgttt tccgacggag    6720
agattgatga gctgagccgc agagtaactg agtccgaacc cgtcctgttt ggatcatttg    6780
aaccgggcga agtgaactca attatatcgt cccgatcagc cgtatctttt ccactacgca    6840
agcagagacg tagacgcagg agcaggagga ctgaatactg actaaccggg gtaggtgggt    6900
acatattttc gacggacaca ggccctgggc acttgcaaaa gaagtccgtt ctgcagaacc    6960
agcttacaga accgaccttg gagcgcaatg tcctggaaag aattcatgcc ccggtgctcg    7020
acacgtcgaa agaggaacaa ctcaaactca ggtaccagat gatgcccacc gaagccaaca    7080
aaagtaggta ccagtctcgt aaagtagaaa atcagaaagc cataaccact gagcgactac    7140
tgtcaggact acgactgtat aactctgcca cagatcagcc agaatgctat aagatcacct    7200
atccgaaacc attgtactcc agtagcgtac cggcgaacta ctccgatcca cagttcgctg    7260
tagctgtctg taacaactat ctgcatgaga actatccgac agtagcatct tatcagatta    7320
```

```
ctgacgagta cgatgcttac ttggatatgg tagacgggac agtcgcctgc ctggatactg    7380
caaccttctg ccccgctaag cttagaagtt acccgaaaaa acatgagtat agagccccga    7440
atatccgcag tgcggttcca tcagcgatgc agaacacgct acaaaatgtg ctcattgccg    7500
caactaaaag aaattgcaac gtcacgcaga tgcgtgaact gccaacactg gactcagcga    7560
cattcaatgt cgaatgcttt cgaaaatatg catgtaatga cgagtattgg gaggagttcg    7620
ctcggaagcc aattaggatt accactgagt tgtcaccgc atatgtagct agactgaaag     7680
gccctaaggc cgccgcacta tttgcaaaga cgtataattt ggtcccattg caagaagtgc    7740
ctatggatag attcgtcatg gacatgaaaa gagacgtgaa agttacacca ggcacgaaac    7800
acacagaaga aagaccgaaa gtacaagtga tacaagccgc agaacccctg gcgactgctt    7860
acttatgcgg gattcaccgg gaattagtgc gtaggcttac ggccgtcttg cttccaaaca    7920
ttcacacgct ttttgacatg tcggcggagg attttgatgc aatcatagca gaacacttca    7980
agcaaggcga cccggtactg gagacggata tcgcatcatt cgacaaaagc caagacgacg    8040
ctatggcgtt aaccggtctg atgatcttgg aggacctggg tgtggatcaa ccactactcg    8100
acttgatcga gtgcgccttt ggagaaatat catccaccca tctacctacg ggtactcgtt    8160
ttaaattcgg ggcgatgatg aaatccggaa tgttcctcac acttttttgtc aacacagttt   8220 tgaatgtcgt tatcgccagc agagtactag aagagcggct taaaacgtcc agatgtgcag    8280
cgttcattgg cgacgacaac atcatacatg gagtagtatc tgacaaagaa atggctgaga    8340
ggtgcgccac ctggctcaac atggaggtta agatcatcga cgcagtcatc ggtgagagac    8400
caccttactt ctgcggcgga tttatcttgc aagattcggt tacttccaca gcgtgccgcg    8460
tggcggaccc cctgaaaagg ctgtttaagt tgggtaaacc gctcccagcc gacgacgagc    8520
aagacgaaga cagaagacgc gctctgctag atgaaacaaa ggcgtggttt agagtaggta    8580
taacaggcac tttagcagtg gccgtgacga cccggtatga ggtagacaat attacacctg    8640
tcctactggc attgagaact tttgcccaga gcaaaagagc attccaagcc atcagagggg    8700
aaataaagca tctctacggt ggtcctaaat agtcagcata gtacatttca tctgactaat    8760
actacaacac caccacctct agcccgggct cgagatctgc gatctaagta agcttggcat    8820
tccggtactg ttggtaaagc caccatggaa gacgccaaaa acataaagaa aggcccggcg    8880
ccattctatc cgctggaaga tggaaccgct ggagagcaac tgcataaggc tatgaagaga    8940
tacgccctgg ttcctggaac aattgctttt acagatgcac atatcgaggt ggacatcact    9000
tacgctgagt acttcgaaat gtccgttcgg ttggcagaag ctatgaaacg atatgggctg    9060
aatacaaatc acagaatcgt cgtatgcagt gaaaactctc ttcaattctt tatgccggtg    9120
ttgggcgcgt tatttatcgg agttgcagtt gcgcccgcga acgacattta taatgaacgt    9180
gaattgctca acagtatggg catttcgcag cctaccgtgg tgttcgtttc caaaaggggg    9240
ttgcaaaaaa ttttgaacgt gcaaaaaaag ctcccaatca tccaaaaaat tattatcatg    9300
gattctaaaa cggattacca gggatttcag tcgatgtaca cgttcgtcac atctcatcta    9360
cctcccggtt ttaatgaata cgattttgtg ccagagtcct tcgatagga caagacaatt    9420 gcactgatca tgaactcctc tggatctact ggtctgccta aaggtgtcgc tctgcctcat    9480
agaactgcct gcgtgagatt ctcgcatgcc agagatccta ttttggcaa tcaaatcatt    9540 ccggatactg cgattttaag tgttgttcca ttccatcacg gttttggaat gtttactaca    9600
ctcggatatt tgatatgtgg atttcgagtc gtcttaatgt atagatttga agaagagctg    9660
tttctgagga gccttcagga ttacaagatt caaagtgcgc tgctggtgcc aaccctattc    9720
```

-continued

```
tccttcttcg ccaaaagcac tctgattgac aaatacgatt tatctaattt acacgaaatt   9780
gcttctggtg gcgctcccct ctctaaggaa gtcggggaag cggttgccaa gaggttccat   9840
ctgccaggta tcaggcaagg atatgggctc actgagacta catcagctat tctgattaca   9900
cccgaggggg atgataaacc gggcgcggtc ggtaaagttg ttccattttt tgaagcgaag   9960
gttgtggatc tggataccgg gaaaacgctg ggcgttaatc aaagaggcga actgtgtgtg  10020
agaggtccta tgattatgtc cggttatgta aacaatccgg aagcgaccaa cgccttgatt  10080
gacaaggatg gatggctaca ttctggagac atagcttact gggacgaaga cgaacacttc  10140
ttcatcgttg accgcctgaa gtctctgatt aagtacaaag ctatcaggt ggctcccgct   10200 gaattggaat ccatcttgct ccaacacccc aacatcttcg acgcaggtgt cgcaggtctt  10260
cccgacgatg acgccggtga acttcccgcc gccgttgttg ttttggagca cggaaagacg  10320
atgacggaaa aagagatcgt ggattacgtc gccagtcaag taacaaccgc gaaaaagttg  10380
cgcggaggag ttgtgtttgt ggacgaagta ccgaaaggtc ttaccggaaa actcgacgca  10440
agaaaaatca gagagatcct cataaaggcc aagaagggcg gaaagatcgc cgtgtaattc  10500
tagaggcgcg ccgatctcac gatcccctga aaaggctgtt taagttgggt aaaccgctcc  10560
cagccgacga cgagcaagac gaagacagaa gacgcgctct gctagatgaa acaaaggcgt  10620
ggtttagagt aggtataaca ggcactttag cagtggccgt gacgacccgg tatgaggtag  10680
acaatattac acctgtccta ctggcattga aacttttgc ccagagcaaa agagcattcc    10740
aagccatcag aggggaaata aagcatctct acggtggtcc taaatagtca gcatagtaca  10800
tttcatctga ctaatactac aacaccacca ccatgaatag aggattcttt aacatgctcg  10860
gccgccgccc cttcccggcc cccactgcca tgtggaggcc gcggagaagg aggcaggcgg  10920
ccccgatgcc tgcccgcaac gggctggctt ctcaaatcca gcaactgacc acagccgtca  10980
gtgccctagt cattggacag gcaactgagc ctcaaccccc acgtccacgc cagccaccgc  11040
gccagaagaa gcaggcgccc aagcaaccac cgaagccgaa gaaaccaaaa acgcaggaga  11100
agaagaagaa gcaacctgca aaacccaaac ccggaaagag acagcgcatg cacttaagt   11160 tggaggccga cagattgttc gacgtcaaga acgaggacgg agatgtcatc gggcacgcac  11220
tggccatgga aggaaaggta atgaaacctc tgcacgtgaa aggaaccatc gaccaccctg  11280
tgctatcaaa gctcaaattt accaagtcgt cagcatacga catggagttc gcacagttgc  11340
cagtcaacat gagaagtgag gcattcacct acaccagtga acaccccgaa ggattctata  11400
actggcacca cggagcggtg cagtatagtg gaggtagatt taccatccct cgcggagtag  11460
gaggcagagg agacagcggt cgtccgatca tggataactc cggtcgggtt gtcgcgatag  11520
tcctcggtgg agctgatgaa ggaacacgaa ctgcccttc ggtcgtcacc tggaatagta    11580
aagggaagac aattaagacg accccggaag ggacagaaga gtggtccgca gcaccactgg  11640
tcacggcaat gtgtttgctc ggaaatgtga gcttcccatg cgaccgcccg cccacatgct  11700 ataccccgcga accttccaga gccctcgaca tccttgaaga aacgtgaac catgaggcct    11760 acgatacccct gctcaatgcc atattgcggt gcggatcgtc tggcagaagc aaaagaagcg  11820
tcatcgatga ctttacccctg accagcccct acttgggcac atgctcgtac tgccaccata  11880
ctgaaccgtg cttcagccct gttaagatcg agcaggtctg ggacgaagcg gacgataaca  11940
ccatacgcat acagacttcc gcccagtttg gatacgacca aagcggagca gcaagcgcaa  12000
acaagtaccg ctacatgtcg cttaagcagg atcacaccgt taaagaaggc accatggatg  12060
acatcaagat tagcacctca ggaccgtgta gaaggcttag ctacaaagga tactttctcc  12120
```

-continued

```
tcgcaaaatg ccctccaggg gacagcgtaa cggttagcat agtgagtagc aactcagcaa    12180
cgtcatgtac actggcccgc aagataaaac caaaattcgt gggacgggaa aaatatgatc    12240
tacctcccgt tcacggtaaa aaaattcctt gcacagtgta cgaccgtctg aaagaaacaa    12300
ctgcaggcta catcactatg cacaggccgg cccgcacgc ttatacatcc tacctggaag     12360
aatcatcagg gaaagtttac gcaaagccgc catctgggaa gaacattacg tatgagtgca    12420
agtgcggcga ctacaagacc ggaaccgttt cgacccgcac cgaaatcact ggttgcaccg    12480
ccatcaagca gtgcgtcgcc tataagagcg accaaacgaa gtgggtcttc aactcaccgg    12540
acttgatccg acatgacgac cacacggtcc aagggaaatt gcatttgcct ttcaagttga    12600
tcccgagtac ctgcatggtc cctgttgccc acgcgccgaa tgtaatacat ggctttaaac    12660
acatcagcct ccaattagat acagaccact tgacattgct caccaccagg agactagggg    12720
caaacccgga accaaccact gaatggatcg tcggaaagac ggtcagaaac ttcaccgtcg    12780
accgagatgg cctggaatac atatggggaa atcatgagcc agtgagggtc tatgcccaag    12840
agtcagcacc aggagaccct cacggatggc cacacgaaat agtacagcat tactaccatc    12900
gccatcctgt gtacaccatc ttagccgtcg catcagctac cgtggcgatg atgattggcg    12960
taactgttgc agtgttatgt gcctgtaaag cgcgccgtga gtgcctgacg ccatacgccc    13020
tggccccaaa cgccgtaatc ccaacttcgc tggcactctt gtgctgcgtt aggtcggcca    13080
atgctgaaac gttcaccgag accatgagtt acttgtggtc gaacagtcag ccgttcttct    13140
gggtccagtt gtgcatacct ttggccgctt tcatcgttct aatgcgctgc tgctcctgct    13200
gcctgccttt tttagtggtt gccggcgcct acctggcgaa ggtagacgcc tacgaacatg    13260
cgaccactgt tccaaatgtg ccacagatac cgtataaggc acttgttgaa agggcagggt    13320
atgccccgct caatttggag atcactgtca tgtcctcgga ggttttgcct tccaccaacc    13380
aagagtacat tacctgcaaa ttcaccactg tggtcccctc cccaaaaatc aaatgctgcg    13440
gctccttgga atgtcagccg gccgttcatg cagactatac ctgcaaggtc ttcggagggg    13500
tctaccccct tatgtgggga ggagcgcaat gttttttgcga cagtgagaac agccagatga    13560
gtgaggcgta cgtcgaactg tcagcagatt gcgcgtctga ccacgcgcag gcgattaagg    13620
tgcacactgc cgcgatgaaa gtaggactgc gtatagtgta cgggaacact accagtttcc    13680
tagatgtgta cgtgaacgga gtcacaccag gaacgtctaa agacttgaaa gtcatagctg    13740
gaccaatttc agcatcgttt acgccattcg atcataaggt cgttatccat cgcggcctgg    13800
tgtacaacta tgacttcccg gaatatggag cgatgaaacc aggagcgttt ggagacattc    13860
aagctaccct cttgactagc aaggatctca tcgccagcac agacattagg ctactcaagc    13920
cttccgccaa gaacgtgcat gtcccgtaca cgcaggccgc atcaggattt gagatgtgga    13980
aaaacaactc aggccgccca ctgcaggaaa ccgcacccct cgggtgtaag attgcagtaa    14040
atccgctccg agcggtggac tgttcatacg ggaacattcc catttctatt gacatcccga    14100
acgctgcctt tatcaggaca tcagatgcac cactggtctc aacagtcaaa tgtgaagtca    14160
gtgagtgcac ttattcagca gacttcggcg ggatggccac cctgcagtat gtatccgacc    14220
gcgaaggtca atgccccgta cattcgcatt cgagcacagc aactctccaa gagtcgacag    14280
tacatgtcct ggagaaagga gcggtgacag tacactttag caccgcgagt ccacaggcga    14340
actttatcgt atcgctgtgt gggaagaaga acaacatgca tgcagaatgt aaaccaccag    14400
ctgaccatat cgtgagcacc ccgcacaaaa atgaccaaga atttcaagcc gccatctcaa    14460
aaacatcatg gagttggctg tttgccctt tcggcggcgc ctcgtcgcta ttaattatag    14520
```

```
gacttatgat ttttgcttgc agcatgatgc tgactagcac acgaagatga ccgctacgcc    14580
ccaatgatcc gaccagcaaa actcgatgta cttccgagga actgatgtgc ataagtgagc    14640
atgcgtttaa actgggccca atgttcccca atgatccgac cagcaaaact cgatgtactt    14700
ccgaggaact gatgtgcata atgcatcagg ctggtacatt agatccccgc ttaccgcggg    14760
caatatagca acactaaaaa ctcgatgtac ttccgaggaa gcgcagtgca taatgctgcg    14820
cagtgttgcc acataaccac tatattaacc atttatctag cggacgccaa aaactcaatg    14880
tatttctgag gaagcgtggt gcataatgcc acgcagcgtc tgcataactt ttattatttc    14940
ttttattaat caacaaaatt ttgttttttaa catttcaaaa aaaaaaaaaa aaaaaaaaaa    15000
aaaaaaaaaa aaaatttaaa ttaattaagc ggccgcctcg aggacgtcag gtggcacttt    15060
tcggggaaat gtgcgcggaa cccctatttg tttatttttc taaatacatt caaatatgta    15120
tccgctcatg agacaataac cctgataaat gcttcaataa tattgaaaaa ggaagagtat    15180
gagtattcaa catttccgtg tcgcccttat tcccttttt gcggcatttt gccttcctgt    15240
ttttgctcac ccagaaacgc tggtgaaagt aaaagatgct gaagatcagt tgggtgcacg    15300
agtgggttac atcgaactgg atctcaacag cggtaagatc cttgagagtt ttcgccccga    15360
agaacgtttt ccaatgatga gcacttttaa agttctgcta tgtggcgcgg tattatcccg    15420
tattgacgcc gggcaagagc aactcggtcg ccgcatacac tattctcaga atgacttggt    15480
tgagtactca ccagtcacag aaaagcatct tacggatggc atgacagtaa gagaattatg    15540
cagtgctgcc ataaccatga gtgataacac tgcggccaac ttacttctga caacgatcgg    15600
aggaccgaag gagctaaccg cttttttgca caacatgggg gatcatgtaa ctcgccttga    15660
tcgttgggaa ccggagctga atgaagccat accaaacgac gagcgtgaca ccacgatgcc    15720
tgtagcaatg gcaacaacgt tgcgcaaact attaactggc gaactactta ctctagcttc    15780
ccggcaacaa ttaatagact ggatggaggc ggataaagtt gcaggaccac ttctgcgctc    15840
ggcccttccg gctggctggt ttattgctga taaatctgga gccggtgagc gtgggtctcg    15900
cggtatcatt gcagcactgg ggccagatgg taagccctcc cgtatcgtag ttatctacac    15960 gacgggagt caggcaacta tggatgaacg aaatagacag atcgctgaga taggtgcctc    16020
actgattaag cattggtaac tgtcagacca agtttactca tatatacttt agattgattt    16080
aaaacttcat ttttaattta aaaggatcta ggtgaagatc cttttttgata atctcatgac    16140 caaaatccct taacgtgagt tttcgttcca ctgagcgtca gaccccgtag aaaagatcaa    16200
aggatcttct tgagatcctt tttttctgcg cgtaatctgc tgcttgcaaa caaaaaaacc    16260
accgctacca gcggtggttt gtttgccgga tcaagagcta ccaactcttt ttccgaaggt    16320
aactggcttc agcagagcgc agataccaaa tactggtctt ctagtgtagc cgtagttagg    16380
ccaccacttc aagaactctg tagcaccgcc tacatacctc gctctgctaa tcctgttacc    16440
agtggctgct gccagtggcg ataagtcgtg tcttaccggg ttggactcaa gacgatagtt    16500
accggataag gcgcagcggt cgggctgaac ggggggttcg tgcacacagc ccagcttgga    16560
gcgaacgacc tacaccgaac tgagatacct acagcgtgag ctatgagaaa gcgccacgct    16620
tcccgaaggg agaaaggcgg acaggtatcc ggtaagcggc agggtcggaa caggagagcg    16680
cacgagggag cttccagggg gaaacgcctg gtatctttat agtcctgtcg ggtttcgcca    16740
cctctgactt gagcgtcgat ttttgtgatg ctcgtcaggg gggcggagcc tatggaaaaa    16800
cgccagcaac gcggcctttt tacggttcct ggccttttgc tggccttttg ctcacatgtg    16860
ggaggctaga gtacatttag gtgacactat agaa                               16894
```

<210> SEQ ID NO 2
<211> LENGTH: 1920
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
atggagaagc cagtagtaaa cgtagacgta gaccccccaga gtccgttttgt cgtgcaactg       60
caaaaaagct ccccgcaatt tgaggtagta gcacagcagg tcactccaaa tgaccatgct      120
aatgccagag cattttcgca tctggccagt aaactaatcg agctggaggt tcctaccaca      180
gcgacgatct tggacatagg cagcgcaccg gctcgtagaa tgttttccga gcaccagtat      240
cattgtgtct gccccatgcg tagtccagaa gacccggacc gcatgatgaa atatgccagt      300
aaactggcgg aaaaagcgtg caagattaca aacaagaact tgcatgagaa gattaaggat      360
ctccggaccg tacttgatac gccggatgct gaaacaccat cgctctgctt tcacaacgat      420
gttacctgca acatgcgtgc cgaatattcc gtcatgcagg acgtgtatat caacgctccc      480
ggaactatct atcatcaggc tatgaaaggc gtgcggaccc tgtactggat tggcttcgac      540
accacccagt tcatgttctc ggctatggca ggttcgtacc ctgcgtacaa caccaactgg      600
gccgacgaga agtccttga agcgcgtaac atcggacttt gcagcacaaa gctgagtgaa      660
ggtaggacag gaaaattgtc gataatgagg aagaaggagt tgaagcccgg gtcgcgggtt      720
tatttctccg taggatcgac actttatcca gaacacagag ccagcttgca gagctggcat      780
cttccatcgg tgttccactt gaatggaaag cagtcgtaca cttgccgctg tgatacagtg      840
gtgagttgcg aaggctacgt agtgaagaaa atcaccatca gtcccgggat cacgggagaa      900
accgtgggat acgcggttac acacaatagc gagggcttct tgctatgcaa agttactgac      960
acagtaaaag gagaacgggt atcgttccct gtgtgcacgt acatcccggc caccatatgc     1020
gatcagatga ctggtataat ggccacggat atatcacctg acgatgcaca aaaacttctg     1080
gttgggctca accagcgaat tgtcattaac ggtaggacta acaggaacac caacaccatg     1140
caaaattacc ttctgccgat catagcacaa gggttcagca atgggctaa ggagcgcaag     1200
gatgatcttg ataacgagaa aatgctgggt actagagaac gcaagcttac gtatggctgc     1260
ttgtgggcgt ttcgcactaa gaaagtacat tcgttttatc gcccacctgg aacgcagacc     1320
atcgtaaaag tccagccctc ttttagcgct tttcccatgt cgtccgtatg gacgacctct     1380
ttgcccatgt cgctgaggca gaaattgaaa ctggcattgc aaccaaagaa ggaggaaaaa     1440
ctgctgcagg tctcggagga attagtcatg gaggccaagg ctgcttttga ggatgctcag     1500
gaggaagcca gagcggagaa gctccgagaa gcacttccac cattagtggc agacaaaggc     1560
atcgaggcag ccgcagaagt tgtctgcgaa gtggaggggc tccaggcgga catcggagca     1620
gcattagttg aaaccccgcg cggtcacgta aggataatac ctcaagcaaa tgaccgtatg     1680
atcggacagt atatcgttgt ctcgccaaac tctgtgctga gaatgccaa actcgcacca     1740
gcgcacccgc tagcagatca ggttaagatc ataacacact ccggaagatc aggaaggtac     1800
gcggtcgaac catacgacgc taaagtactg atgccagcag aggtgccgt accatggcca     1860
gaattcctag cactgagtga gagcgccacg ttagtgtaca cgaaagaga gtttgtgaac     1920
```

<210> SEQ ID NO 3
<211> LENGTH: 2121
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
cgcaaactat accacattgc catgcatggc cccgccaaga atacagaaga ggagcagtac      60
aaggttacaa aggcagagct tgcagaaaca gagtacgtgt ttgacgtgga caagaagcgt     120
tgcgttaaga aggaagaagc ctcaggtctg gtcctctcgg gagaactgac caaccctccc     180
tatcatgagc tagctctgga gggactgaag acccgacctg cggtcccgta caaggtcgaa     240
acaataggag tgataggcac accggggtcg ggcaagtcag ctattatcaa gtcaactgtc     300
acggcacgag atcttgttac cagcggaaag aaagaaaatt gtcgcgaaat tgaggccgac     360
gtgctaagac tgagggggtat gcagattacg tcgaagacga tagattcggt tatgctcaac     420
ggatgccaca aagccgtaga agtgctgtac gttgacgaag cgttcgcgtg ccacgcagga    480
gcactacttg ccttgattgc tatcgtcagg ccccgcaaga aggtagtact atgcggagac    540
cccatgcaat gcggattctt caacatgatg caactaaagg tacatttcaa tcaccctgaa    600
aaagacatat gcaccaagac attctacaag tatatctccc ggcgttgcac acagccagtt    660
acagctattg tatcgacact gcattacgat ggaaagatga aaaccacgaa cccgtgcaag    720
aagaacattg aaatcgatat tacaggggcc acaaagccga agccagggga tatcatcctg    780
acatgttttc gcgggtgggt taagcaattg caaatcgact atcccggaca tgaagtaatg    840
acagccgcgg cctcacaagg gctaaccaga aaaggagtgt atgccgtccg gcaaaaagtc    900
aatgaaaacc cactgtacgc gatcacatca gagcatgtga acgtgttgct cacccgcact    960
gaggacaggc tagtgtggaa accttgcag ggcgacccat ggattaagca gctcactaac     1020
atacctaaag gaaactttca ggctactata gaggactggg aagctgaaca aagggaata    1080
attgctgcaa taaacagccc cactcccgt gccaatccgt tcagctgcaa gaccaacgtt    1140
tgctgggcga aagcattgga accgatacta gccacggccg gtatcgtact taccggttgc    1200
cagtggagcg aactgttccc acagtttgcg gatgacaaac cacattcggc catttacgcc    1260
ttagacgtaa tttgcattaa gttttcggc atggacttga caagcggact gttttctaaa    1320
cagagcatcc cactaacgta ccatcccgcc gattcagcga ggccggtagc tcattgggac    1380
aacagcccag gaacccgcaa gtatgggtac gatcacgcca ttgccgccga actctcccgt    1440
agatttccgg tgttccagct agctgggaag gcacacaac ttgatttgca gacggggaga    1500
accagagtta tctctgcaca gcataacctg gtcccggtga accgcaatct tcctcacgcc    1560
ttagtccccg agtacaagga gaagcaaccc ggcccggtcg aaaaattctt gaaccagttc    1620
aaacaccact cagtacttgt ggtatcagag gaaaaaattg aagctccccg taagagaatc    1680
gaatggatcg ccccgattgg catagccggt gcagataaga actacaacct ggctttcggg    1740
tttccgccgc aggcacggta cgacctggtt ttcatcaaca ttggaactaa atacagaaac    1800
caccacttc agcagtgcga agaccatgcg gcgaccttaa aaacccttc gcgttcggcc    1860
ctgaattgcc ttaacccagg aggcacccctc gtggtgaagt cctatggcta cgccgaccgc    1920
aacagtgagg acgtagtcac cgctcttgcc agaaagtttg tcagggtgtc tgcagcgaga    1980
ccagattgtg tctcaagcaa tacagaaatg tacctgattt tccgacaact agacaacagc    2040
cgtacacggc aattcacccc gcaccatctg aattgcgtga tttcgtccgt gtatgagggt    2100
acaagagatg gagttggagc c                                             2121
```

<210> SEQ ID NO 4

<211> LENGTH: 1641
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

| | | | | | |
|---|---|---|---|---|---|
| gcgccgtcat | accgcaccaa | aagggagaat | attgctgact | gtcaagagga | agcagttgtc | 60 |
| aacgcagcca | atccgctggg | tagaccaggc | gaaggagtct | gccgtgccat | ctataaacgt | 120 |
| tggccgacca | gttttaccga | ttcagccacg | gagacaggca | ccgcaagaat | gactgtgtgc | 180 |
| ctaggaaaga | aagtgatcca | cgcggtcggc | cctgatttcc | ggaagcaccc | agaagcagaa | 240 |
| gccttgaaat | tgctacaaaa | cgcctaccat | gcagtggcag | acttagtaaa | tgaacataac | 300 |
| atcaagtctg | tcgccattcc | actgctatct | acaggcattt | acgcagccgg | aaaagaccgc | 360 |
| cttgaagtat | cacttaactg | cttgacaacc | gcgctagaca | gaactgacgc | ggacgtaacc | 420 |
| atctattgcc | tggataagaa | gtggaaggaa | agaatcgacg | cggcactcca | acttaaggag | 480 |
| tctgtaacag | agctgaagga | tgaagatatg | gagatcgacg | atgagttagt | atggatccat | 540 |
| ccagacagtt | gcttgaaggg | aagaaaggga | ttcagtacta | caaaaggaaa | attgtattcg | 600 |
| tacttcgaag | gcaccaaatt | ccatcaagca | gcaaaagaca | tggcggagat | aaaggtcctg | 660 |
| ttccctaatg | accaggaaag | taatgaacaa | ctgtgtgcct | acatattggg | tgagaccatg | 720 |
| gaagcaatcc | gcgaaaagtg | cccggtcgac | cataaccgt | cgtctagccc | gcccaaaacg | 780 |
| ttgccgtgcc | tttgcatgta | tgccatgacg | ccagaaaggg | tccacagact | agaagcaat | 840 |
| aacgtcaaag | aagttacagt | atgctcctcc | acccccttc | ctaagcacaa | aattaagaat | 900 |
| gttcagaagg | ttcagtgcac | gaaagtagtc | ctgtttaatc | cgcacactcc | cgcattcgtt | 960 |
| cccgccgta | agtacataga | agtgccagaa | cagcctaccg | ctcctcctgc | acaggccgag | 1020 |
| gaggcccccg | aagttgtagc | gacaccgtca | ccatctacag | ctgataacac | ctcgcttgat | 1080 |
| gtcacagaca | tctcactgga | tatggatgac | agtagcgaag | gctcactttt | ttcgagcttt | 1140 |
| agcggatcgg | acaactctat | tatggacagt | tggtcgtcag | gacctagttc | actagagata | 1200 |
| gtagaccgaa | ggcaggtggt | ggtggctgac | gttcatgccg | tccaagagcc | tgccctatt | 1260 |
| ccaccgccaa | ggctaaagaa | gatggcccgc | ctggcagcgg | caagaaaaga | gcccactcca | 1320 |
| ccggcaagca | atagctctga | gtccctccac | ctctcttttg | gtggggtatc | catgtccctc | 1380 |
| ggatcaattt | tcgacggaga | gacggcccgc | caggcagcgg | tacaaccct | ggcaacaggc | 1440 |
| cccacggatg | tgcctatgtc | tttcggatcg | ttttccgacg | gagagattga | tgagctgagc | 1500 |
| cgcagagtaa | ctgagtccga | acccgtcctg | tttggatcat | ttgaaccggg | cgaagtgaac | 1560 |
| tcaattatat | cgtcccgatc | agccgtatct | tttccactac | gcaagcagag | acgtagacgc | 1620 |
| aggagcagga | ggactgaata | c | | | | 1641 |

<210> SEQ ID NO 5
<211> LENGTH: 1851
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

| | | | | | |
|---|---|---|---|---|---|
| tgactaaccg | gggtaggtgg | gtacatattt | tcgacggaca | caggccctgg | gcacttgcaa | 60 |
| aagaagtccg | ttctgcagaa | ccagcttaca | gaaccgacct | tggagcgcaa | tgtcctggaa | 120 |

```
agaattcatg ccccggtgct cgacacgtcg aaagaggaac aactcaaact caggtaccag    180
atgatgccca ccgaagccaa caaaagtagg taccagtctc gtaaagtaga aaatcagaaa    240
gccataacca ctgagcgact actgtcagga ctacgactgt ataactctgc cacagatcag    300
ccagaatgct ataagatcac ctatccgaaa ccattgtact ccagtagcgt accggcgaac    360
tactccgatc cacagttcgc tgtagctgtc tgtaacaact atctgcatga aactatccg     420 acagtagcat cttatcagat tactgacgag tacgatgctt acttggatat ggtagacggg    480
acagtcgcct gcctggatac tgcaaccttc tgccccgcta agcttagaag ttacccgaaa    540
aaacatgagt atagagcccc gaatatccgc agtgcggttc catcagcgat gcagaacacg    600
ctacaaaatg tgctcattgc cgcaactaaa agaaattgca acgtcacgca gatgcgtgaa    660
ctgccaacac tggactcagc gacattcaat gtcgaatgct ttcgaaaata tgcatgtaat    720
gacgagtatt gggaggagtt cgctcggaag ccaattagga ttaccactga gtttgtcacc    780
gcatatgtag ctagactgaa aggccctaag gccgccgcac tatttgcaaa gacgtataat    840
ttggtcccat tgcaagaagt gcctatggat agattcgtca tggacatgaa agagacgtg     900 aaagttacac caggcacgaa acacacagaa gaaagaccga agtacaagt gatacaagcc     960 gcagaacccc tggcgactgc ttacttatgc gggattcacc gggaattagt gcgtaggctt   1020
acggccgtct tgcttccaaa cattcacacg cttttttgaca tgtcggcgga ggattttgat   1080
gcaatcatag cagaacactt caagcaaggc gacccggtac tggagacgga tatcgcatca   1140
ttcgacaaaa gccaagacga cgctatggcg ttaaccggtc tgatgatctt ggaggacctg   1200
ggtgtggatc aaccactact cgacttgatc gagtgcgcct ttggagaaat atcatccacc   1260
catctaccta cgggtactcg ttttaaattc ggggcgatga tgaaatccgg aatgttcctc   1320 acacttttg tcaacacagt tttgaatgtc gttatcgcca gcagagtact agaagagcgg    1380
cttaaaacgt ccagatgtgc agcgttcatt ggcgacgaca acatcataca tggagtagta   1440
tctgacaaag aaatggctga gaggtgcgcc acctggctca acatggaggt taagatcatc   1500
gacgcagtca tcggtgagag accaccttac ttctgcggcg gatttatctt gcaagattcg   1560
gttacttcca cagcgtgccg cgtggcggac cccctgaaaa ggctgtttaa gttgggtaaa   1620
ccgctcccag ccgacgacga gcaagacgaa gacagaagac gcgctctgct agatgaaaca   1680
aaggcgtggt ttagagtagg tataacaggc actttagcag tggccgtgac gacccggtat   1740
gaggtagaca atattacacc tgtcctactg gcattgagaa cttttgccca gagcaaaaga   1800
gcattccaag ccatcagagg ggaaataaag catctctacg gtggtcctaa a           1851
```

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gtcctaaata gtc                                                        13

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 7
tctctacggt ggtcctaaat agtc                                         24

<210> SEQ ID NO 8
<211> LENGTH: 3735
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
atgaatagag gattctttaa catgctcggc cgccgcccct cccggcccc cactgccatg        60 tggaggccgc ggagaaggag gcaggcggcc ccgatgcctg cccgcaacgg gctggcttct     120
caaatccagc aactgaccac agccgtcagt gccctagtca ttggacaggc aactagacct     180 caaccccac gtccacgcca gccaccgcgc cagaagaagc aggcgcccaa gcaaccaccg      240
aagccgaaga accaaaaac gcaggagaag aagaagaagc aacctgcaaa acccaaaccc     300
ggaaagagac agcgcatggc acttaagttg gaggccgaca gattgttcga cgtcaagaac     360
gaggacggag atgtcatcgg gcacgcactg gccatggaag gaaaggtaat gaaacctctg     420
cacgtgaaag gaaccatcga ccaccctgtg ctatcaaagc tcaaatttac caagtcgtca     480
gcatacgaca tggagttcgc acagttgcca gtcaacatga agtgaggc attcacctac       540 accagtgaac ccccgaagg attctataac tggcaccacg gagcggtgca gtatagtgga     600
ggtagattta ccatccctcg cggagtagga ggcagaggac agcggtcg tccgatcatg       660 gataactccg gtcgggttgt cgcgatagtc ctcggtggag ctgatgaagg aacacgaact     720
gccctttcgg tcgtcacctg gaatagtaaa gggaagacaa ttaagacgac cccggaaggg     780
acagaagagt ggtccgcagc accactggtc acggcaatgt gtttgctcgg aaatgtgagc     840
ttcccatgcg accgcccgcc cacatgctat cccgcgaac cttccagagc cctcgacatc      900
cttgaagaga acgtgaacca tgaggcctac gatacccctgc tcaatgccat attgcggtgc     960
ggatcgtctg gcagaagcaa aagaagcgtc atcgatgact ttaccctgac cagcccctac    1020
ttgggcacat gctcgtactg ccaccatact gaaccgtgct tcagccctgt taagatcgag    1080
caggtctggg acgaagcgga cgataacacc atacgcatac agacttccgc ccagtttgga    1140
tacgaccaaa gcggagcagc aagcgcaaac aagtaccgct acatgtcgct taagcaggat    1200
cacaccgtta agaaggcac catggatgac atcaagatta gcacctcagg accgtgtaga    1260
aggcttagct acaaaggata ctttctcctc gcaaaatgcc ctccagggga cagcgtaacg    1320
gttagcatag tgagtagcaa ctcagcaacg tcatgtacac tggcccgcaa gataaaacca    1380
aaattcgtgg gacgggaaaa atatgatcta cctcccgttc acggtaaaaa aattccttgc    1440
acagtgtacg accgtctgaa agaaacaact gcaggctaca tcactatgca caggccgggc    1500
ccgcacgctt atacatccta cctggaagaa tcatcaggga agtttacgc aaagccgcca    1560 tctgggaaga acattacgta tgagtgcaag tgcggcgact acaagaccgg aaccgttttcg    1620 acccgcaccg aaatcactgg ttgcaccgcc atcaagcagt gcgtcgccta aagagcgac    1680 caaacgaagt gggtcttcaa ctcaccggac ttgatccgac atgacgacca cacggtccaa    1740
gggaaattgc atttgccttt caagttgatc ccgagtacct gcatggtccc tgttgcccac    1800
gcgccgaatg taatacatgg cttaaacac atcagcctcc aattagatac agaccacttg    1860
acattgctca ccaccaggag actaggggca aacccggaac caaccactga atggatcgtc    1920
ggaaagacgg tcagaaactt caccgtcgac cgagatggcc tggaatacat atggggaaat    1980
```

```
catgagccag tgagggtcta tgcccaagag tcagcaccag gagaccctca cggatggcca    2040
cacgaaatag tacagcatta ctaccatcgc catcctgtgt acaccatctt agccgtcgca    2100
tcagctaccg tggcgatgat gattggcgta actgttgcag tgttatgtgc ctgtaaagcg    2160
cgccgtgagt gcctgacgcc atacgccctg gccccaaacg ccgtaatccc aacttcgctg    2220
gcactcttgt gctgcgttag gtcggccaat gctgaaacgt tcaccgagac catgagttac    2280
ttgtggtcga acagtcagcc gttcttctgg gtccagttgt gcatacctttt ggccgctttc    2340 atcgttctaa tgcgctgctg ctcctgctgc ctgccttttt tagtggttgc cggcgcctac    2400
ctggcgaagg tagacgccta cgaacatgcg accactgttc caaatgtgcc acagataccg    2460
tataaggcac ttgttgaaag ggcagggtat gccccgctca atttggagat cactgtcatg    2520
tcctcggagg ttttgccttc caccaaccaa gagtacatta cctgcaaatt caccactgtg    2580
gtcccctccc caaaaatcaa atgctgcggc tccttggaat gtcagccggc cgttcatgca    2640
gactatacct gcaaggtctt cggagggtc taccccttta tgtggggagg agcgcaatgt    2700
ttttgcgaca gtgagaacag ccagatgagt gaggcgtacg tcgaactgtc agcagattgc    2760
gcgtctgacc acgcgcaggc gattaaggtg cacactgccg cgatgaaagt aggactgcgt    2820
atagtgtacg ggaacactac cagtttccta gatgtgtacg tgaacggagt cacaccagga    2880
acgtctaaag acttgaaagt catagctgga ccaatttcag catcgtttac gccattcgat    2940
cataaggtcg ttatccatcg cggcctggtg tacaactatg acttcccgga atatggagcg    3000
atgaaaccag gagcgtttgg agacattcaa gctacctcct tgactagcaa ggatctcatc    3060
gccagcacag acattaggct actcaagcct tccgccaaga acgtgcatgt cccgtacacg    3120
caggccgcat caggatttga gatgtggaaa aacaactcag gccgcccact gcaggaaacc    3180
gcacctttcg ggtgtaagat tgcagtaaat ccgctccgag cggtggactg ttcatacggg    3240
aacattccca tttctattga catcccgaac gctgccttta tcaggacatc agatgcacca    3300
ctggtctcaa cagtcaaatg tgaagtcagt gagtgcactt attcagcaga cttcggcggg    3360
atggccaccc tgcagtatgt atccgaccgc gaaggtcaat gccccgtaca ttcgcattcg    3420
agcacagcaa ctctccaaga gtcgacagta catgtcctgg agaaaggagc ggtgacagta    3480
cactttagca ccgcgagtcc acaggcgaac tttatcgtat cgctgtgtgg gaagaagaca    3540
acatgcaatg cagaatgtaa accaccagct gaccatatcg tgagcacccc gcacaaaaat    3600
gaccaagaat ttcaagccgc catctcaaaa acatcatgga gttggctgtt tgccctttc    3660 ggcggcgcct cgtcgctatt aattatagga cttatgattt ttgcttgcag catgatgctg    3720
actagcacac gaaga                                                     3735
```